US007640113B2

(12) United States Patent
Frudakis et al.

(10) Patent No.: US 7,640,113 B2
(45) Date of Patent: Dec. 29, 2009

(54) METHODS AND APPARATUS FOR COMPLEX GENETICS CLASSIFICATION BASED ON CORRESPONDENCE ANALYSIS AND LINEAR/QUADRATIC ANALYSIS

(75) Inventors: Tony Nick Frudakis, Sarasota, FL (US); Venkateswarlu Kondragunta, Sarasota, FL (US); Sivamani Natarajan, Sarasota, FL (US)

(73) Assignee: DNAPrint Genomics, Inc., Sarasota, FL (US)

( * ) Notice: Subject to any disclaimer, the term of this patent is extended or adjusted under 35 U.S.C. 154(b) by 0 days.

(21) Appl. No.: 10/495,962

(22) PCT Filed: Dec. 2, 2002

(86) PCT No.: PCT/US02/41465

§ 371 (c)(1),
(2), (4) Date: Sep. 20, 2004

(87) PCT Pub. No.: WO03/048372

PCT Pub. Date: Jun. 12, 2003

(65) Prior Publication Data

US 2005/0149271 A1    Jul. 7, 2005

Related U.S. Application Data

(60) Provisional application No. 60/338,524, filed on Dec. 3, 2001, provisional application No. 60/338,468, filed on Dec. 3, 2001, provisional application No. 60/377,164, filed on May 2, 2002.

(51) Int. Cl.
*G06F 19/00* (2006.01)
(52) U.S. Cl. ....................................................... 702/19
(58) Field of Classification Search ....................... None
See application file for complete search history.

(56) References Cited

U.S. PATENT DOCUMENTS 5,541,067 A   7/1996   Perlin
6,291,182 B1  9/2001   Schork et al.

OTHER PUBLICATIONS

Weintrob N et al, 'Type 1 diabetes environmental factors and correspondence analysis of HLA dass II genes in the Yemenite Jewish Community in Israel, Diabetes Care 2001 United States, vol. 24, No. 4, Apr. 2001, pp. 650-653.

Mayer S, et al., "Haplotype Study of the HLA-A,B,C and Bf Associations by the Factorial Correspondence Analysis", Journal of Immungenetics, vol. 8, No. 1, 1981. pp. 7-14.

M.J. Greenacre, L Degos: "Correspondence Analysis of HLA Gene Frequency Data from 124 Population Samples", American Society of Human Genetics, 1977, pp. 60-75.

Lucek Paul et al., "Multi-locus nonparametric linkage analysis of complex trait loci with neural networks", Human Heredity, vol. 48, No. 5, Sep. 1998, pp. 275-284.

Fellenberg Kurt et al, "Correspondence analysis applied to microarray data", Proceedings of the National Academy of Sciences of the United States, vol. 98, No. 19, Sep. 11, 2001, pp. 10781-10786.

Tertwilliger J D et al, "Gene mapping in the 20th and 21st centuries: statistical methods, data analysis and experimental design" Human Biology, XX XX, vol. 72, No. 1, Feb. 2000, pp. 63-132.

Lander and Kruglyak, "Genetic Dissection of Complex Traits: Guidelines For Interpreting and Reporting Linkage Results", Nature Genetics, New York, NY, US, vol. 11, Nov. 1995, pp. 241-247.

J.S. Palmer et al., "Melanocortin-1 Receptor Polymorphisms and Risk of Melanoma: Is the Association Explained Solely by Pigmentation Phenotype?", AM> J. Hum. Genet., vol. 66, 2000, pp. 176-186.

PCT International Application No. PCT/US02/38309; Frudakis; Entitled "Method and Apparatus for Use in Genetics Classification Including Classification Tree Analysis".

PCT International Application No. PCT/US02/38326; Frudakis; Entitled "Methods for the Identification of Genetic Features for Complex Genetics Classifiers".

Kishino, Hirohisa; Waddell, Peter J.; "Correspondence Analysis of Genes and Tissue Types and Finding Genetic Links form Microarray Data", Genome Informatics 11, 2000, pp. 83-95, Japan.

Fellenberg, Kurt; Busold, Christian, "Correspondence Analysis and Data Warehousing with Microarray Data", Jun. 23, 2004, pp. 1-12.

*Primary Examiner*—Lori A Clow
(74) *Attorney, Agent, or Firm*—John J. Oskorep, Esq.

(57) ABSTRACT

Methods and apparatus for use in complex genetics classification are disclosed. In one illustrative example, a method is performed using data from a sample population which includes counts of individuals in the sample population associated with both a particular diploid haplotype pair and a particular genetic trait class. A correspondence to analysis (COA) on the data from the sample population is performed (at least in part) so as to determine a first plurality of n-dimensional coordinates for each diploid haplotype pair and a second plurality of n-dimensional coordinates for each genetic trait class. A linear or quadratic classification analysis is then performed based on the first and the second pluralities of n-dimensional coordinates and diploid haplotype pairs of the at least two genes from an individual sample. Advantageously, the individual sample can be accurately classified into one of the genetic trait classes using the method.

24 Claims, 10 Drawing Sheets

|  |  | POSITION |  |  |  |  |  |  |  | |
|---|---|---|---|---|---|---|---|---|---|---|
| INDIVIDUAL |  | 1 | 2 | 3 | 4 | 5 | 6 | 7 | 8 | STATUS |
| PERSON 1 | HAPLOTYPE 1 | G | C | A | T | G | A | C | T | NON-RESPONDER |
|  | HAPLOTYPE 2 | C | C | T | T | A | G | C | G |  |
| PERSON 2 | HAPLOTYPE 1 | G | G | A | T | G | A | C | T | RESPONDER |
|  | HAPLOTYPE 2 | C | G | T | T | A | G | C | G |  |
| PERSON 3 | HAPLOTYPE 1 | G | C | A | T | G | A | C | T | NON-RESPONDER |
|  | HAPLOTYPE 2 | C | C | T | T | A | G | C | G |  |
| PERSON 4 | HAPLOTYPE 1 | G | G | A | T | G | A | C | T | RESPONDER |
|  | HAPLOTYPE 2 | C | G | T | T | A | G | C | G |  |

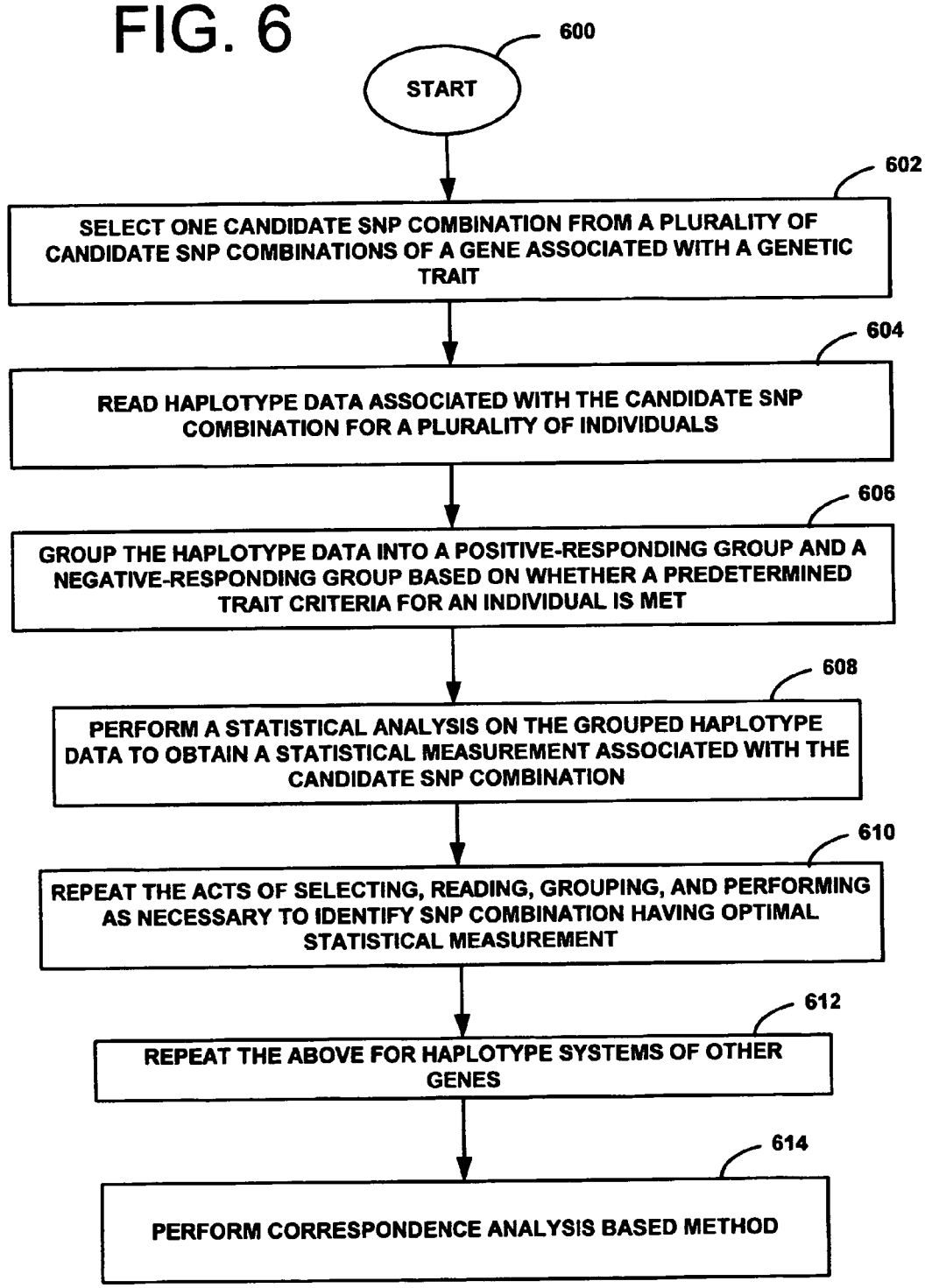

METHODS AND APPARATUS FOR COMPLEX GENETICS CLASSIFICATION BASED ON CORRESPONDENCE ANALYSIS AND LINEAR/QUADRATIC ANALYSIS

CROSS-REFERENCE TO RELATED APPLICATIONS

This application is a national phase filing under 35 U.S.C. Sect. 371 of PCT International Application Number PCT/US02/41465 having an International Filing Date of Dec. 2, 2002, and claiming earlier priority to a U.S. Provisional Patent Application having U.S. Ser. No. 60/338,524, a filing date of Dec. 3, 2001, and a title of "A Correspondence Method For Constructing Complex Genetics Classifiers"; a U.S. Provisional Patent Application having U.S. Ser. No. 60/338,468, a filing date of Dec. 3, 2001, and a title of "Linear And Quadratic Methods For Constructing Complex Genetics Classifiers"; and a U.S. Provisional Patent Application having U.S. Ser. No. 60/377,164, a filing date of May 2, 2002, and a title of "Combined Correspondence Analysis And Linear/Quadratic Analysis For Constructing Complex Genetics Classifiers", all of which are hereby incorporated by reference herein.

TECHNICAL FIELD

The present invention relates generally to genetics classification, and relates more particularly to methods and apparatus for complex genetics classification based on statistical analyses of sample populations.

BACKGROUND INFORMATION

The purpose of genetics classification is to be able to accurately classify individuals into one of a plurality of trait classes (e.g. brown, blue, green, etc.) associated with a particular genetic trait (e.g. eye color). The present application relates to the use of complex genetics analysis and software to create or construct accurate genetics classification tests. Such classification tests have valuable applications, especially in the fields of personalized medicine and criminal forensics.

Human beings differ only by up to 0.1% of the three billion letters of DNA present in the human genome. Though we are 99.9% identical in genetic sequence, it is the 0.1% that determines our uniqueness. Our individuality is apparent from visual inspection—almost anyone can recognize that people have different facial features, heights and colors, and that these features are, to some extent, heritable (e.g. sons and daughters tend to resemble their parents more than strangers do).

Few realize, however, that our individuality extends to an ability or inability to respond to and metabolize particular drugs. Drugs are referred to as "xenobiotics" because they are chemical compounds that are not naturally found in the human body. Xenobiotic metabolism genes make proteins whose sole purpose is to detoxify foreign compounds present in the human body, and they evolved to allow humans to degrade and excrete harmful chemicals present in many foods (such as tannins and alkaloids from which many drugs are derived).

Because variability in drug metabolism enzyme sequences is known to explain most of the variability in drug response, it can be tested whether single nucleotide polymorphisms (SNPs) within the common xenobiotic metabolism genes are linked to variable drug response. To do this, thousands of SNP markers in hundreds of xenobiotic metabolism genes can be surveyed. From learning why some people respond well to a drug (i.e. they have certain SNPs) while others do not (i.e. they do not have the certain SNPs), classifier tests can be developed. Classifier tests include chemicals called "probes" that help determine the sequence of a person at the SNP letters. The classifier test can determine the suitability of the patient for a drug before it is ever prescribed. This is commonly referred to as a "personalized drug prescription".

Detailed analyses of SNPs and haplotype systems are required prior to developing these tests. A "haplotype system" is a coined term in the present application which describes the set of diploid (2 per person) phase-known haplotype combinations of alleles for a given set of SNP loci. A haplotype may be viewed as a particular gene flavor. Just as there are many flavors of candy in a candy store, there are many gene flavors in the human population. "Phase" refers to a linear string of sequence along a chromosome. Humans have two copies of each chromosome, one derived from the mother and one derived from the father.

Assume that a person has, in their genome, the diploid sequences shown below in Text Illustration 1.

TEXT ILLUSTRATION 1

A hypothetical string of DNA sequence in a hypothetical person.

| Position | 1 2 3 4 5 6 7 8 9 10 11 12 13 14 |
|---|---|
| Person 1: | A G T C T G C C C A T G G |
|  | A C T C T G C C C A A T G G |

The "sense strand" is shown for both the paternal and maternal chromosome. This pair of sequences is called a diploid pair which represents a small segment of the three billion nucleotide letters that make up the individual's genome. Positions 2 and 8 indicate positions where people (and in fact this person) exhibit variability. Each position of variability is known as a SNP (single nucleotide polymorphism), and there are two of them shown in Text Illustration 1. Assume that positions 2 and 8 are the only SNPs in this region of the human genome. In this case, people are identical in genetic sequence at all other letters in the string. Thus, in the entire human race, only an A is observed at position 1, either a G or a C at position 2, only a T at position 3, and so on. By convention, person 1 is called a G/C heterozygote at SNP1 and a C/A heterozygote at SNP2.

Text Illustration 1 can be re-written as shown below in Text Illustration 2.

TEXT ILLUSTRATION 2

A more convenient way to represent Person 1 than Text Illustration 1, where only the variable nucleotides are shown. The GC refers to the sequence of Person 1's maternal chromosome (reading the sense strand only) and the CA refers to the sequence of Person 1's paternal chromosome (reading the sense strand only).

| Person 1: | GC |
|---|---|
|  | CA |

In Text Illustration 2, the non-SNP nucleotide positions are omitted for convenience. Text Illustration 2 conveys every bit as much information about the sequence of Person 1 as does Text Illustration 1, because it is assumed in genetics that unwritten nucleotides are not variable. Although there are seven nucleotide letters in between SNP 1 (at position 2) and SNP 2 (at position 8), they are the same in everybody and are therefore already known by de facto by reference to the consensus human genome sequence for the region represented by the sequence.

The genotype in Text Illustration 2 can be represented in even another way shown below in Text Illustration 3.

TEXT ILLUSTRATION 3

Haplotype pair as written by convention for Person 1.

Person 1:            GC/CA

The sequences GC and CA are called haplotypes. Person 1, as does everyone, has two haplotypes: one GC haplotype and one CA haplotype. Thus, this individual can be referred to as a GC/CA individual. One haplotype is derived from the mother (maternal) and the other is derived from their father (paternal). It is not known from this representation whether the paternal haplotype is the GC or the CA haplotype.

When a scientist reads genetic data from people, they generally only read the positions that are different from person to person. This process is called "genotyping". Although it would be very convenient to read that person 1 has a GC sequence in this region of their maternal chromosome and a CA sequence at their paternal chromosome, it is most practical technically to read the diploid pair of nucleotide letters at SNP 1 and the diploid pair of letters at SNP2 independently.

What a scientist reads, therefore, is shown below in Text Illustration 4.

TEXT ILLUSTRATION 4

Genotype reading from Person 1.
The person has a G and a C at SNP1, and a C and an A at SNP2.

Person 1:    SNP1: (G/C)    SNP2: (C/A)

From Text Illustrations 1, 2, and 3 it can be seen that the person is a GC/CA individual, as written by genetic convention. From the representation shown in Text Illustration 4, however, this is more difficult to identify since the SNP genotypes can be combined in several different ways. For example, it is not known whether the individual has the GC/CA haplotype pair or the GA/CC haplotype pair; all that is known is that the individual has a G and C at SNP1 and a C and A at SNP2. It is possible, however, to use well-known statistical methods to infer that the person indeed harbors the GC/CA haplotype pair rather than the GA/CC pair (i.e. Stephens, M., Smith, N. and P. Donnelly. (2001). A new statistical method for haplotype reconstruction from population data. Am. J. Hum. Genet. 68:978-989.). So inferring, Text Illustration 4 contains every bit of information as do Text Illustrations 1 through 3. The genotypes shown in Text Illustration 4 are called "phase-unknown" genotypes because it is not clear (before inference) whether the SNP genotypes are components of GC/CA or GA/CC haplotype pairs. After the phase has been determined as GC and CA, each haplotype is referred to as a "phase-known" genotype pair.

By definition, haplotypes are comprised of phase-known genotype combinations. Haplotype pairs are comprised of pairs of phase-known genotype combinations. In the example given (Text Illustrations 1-4), there are 2 SNPs within a stretch of 14 nucleotide letters of DNA from a particular segment of the genome. In actual practice, however, genes are much longer than 14 nucleotide letters long and a SNP is generally found once every few hundred nucleotide letters.

Regardless of its length in nucleotide letters, a gene containing 4 SNPs has a large number of 2-locus haplotype systems, a smaller number of 3-locus haplotype systems, and one 4 locus haplotype system. In FIG. 1, a gene 100 with a plurality of SNPs 102 is illustrated in a second example to help describe the concepts regarding a haplotype system. In this second example, gene 100 is one thousand nucleotides long and shown as a horizontal block. Arrows which extend from SNPs 102 to gene 100 identify four nucleotide positions within the gene sequence that may be different in different individuals. On the other hand, the remaining 996 nucleotides are identical in different individuals of the world population. Virtually all known SNP loci are bi-allelic, meaning that there are only two possible nucleotides found at that position in the population.

For the purposes of this example, the bi-allelic sites will be defined as SNP1=(A/T), SNP2=(G/A), SNP3=(C/T) and SNP4=(C/T). Given the laws of probability, this gene 100 has $2^4 = 16$ possible haplotype systems. One of these haplotype systems is:

SNP1:SNP2:SNP3:SNP4 which is a four-locus haplotype system. Given that SNP1=(A/T), SNP2=(G/A), SNP3=(C/T), and SNP4=(C/T), there are several constituent haplotypes that are part of this haplotype system. For example:

AGCC

AGTT

TGCC etc.

Another haplotype system (a two-locus system) is:
SNP2:SNP4

Given that SNP1=(A/T), SNP2=(G/A), SNP3=(C/T) and SNP4=(C/T), there are several constituent haplotypes that are part of this particular haplotype system:

GC

GT

AC

AT

Each one of these haplotype systems has many different haplotype constituents that can be combined into an even larger number of haplotype pairs. For example, the SNP2:SNP4 haplotype system contains the GC/GC pair, the GC/GT pair, the GC/AC pair, etc.

Because dispersive genetic forces such as recombination have shaped the genetic structure of the population, the sequence at one SNP is assumed to be independent of the sequence at other SNPs as a base assumption. This means that there are several possible haplotypes in the population of human beings for an N-locus haplotype system. In fact, from probability theory there are $2^N$ possibilities. For example, for a four-locus haplotype system where position 1 is A/T, position 2 is G/A, position 3 is C/T, and position 4 is C/T, there are $2^4=16$ possibilities:

```
AGCC, AGCT, AGTC, AGTT, AACC, AACT, AATC, AATT
TGCC, TGCT, TGTC, TGTT, TACC, TACT, TATC, TATT
```

In actual practice, however, there are usually fewer haplotypes in the population than one would expect because systematic genetic forces (such as population bottlenecks, random genetic drift and selection) have also contributed to shape the structure of our population. This complication will be ignored as it does not significantly impact the present analysis.

As described earlier, a given individual has both a maternal and paternal copy of each chromosome to form a diploid pair. The genotype of any human being, with respect to the haplotype system, is written as a pair. A person written as AGCC/TATT, for example, contains one haplotype derived from the father and one from the mother. Since there are 16 possible haplotypes, there are $$\Sigma[(n)+(n-1)]=124$$

possible diploid haplotype combinations in the human population. Thus, from 4 SNPs, we see how there can be 124 types of people in the population; some are AGCC/AGCC, others are AGCC/AGCT, others AGCC/AGTT, and so on. When the number of SNPs is larger than 4, the numbers quickly become unmanageable. For example, if there are 8 SNPs in a gene, there are 256 possible haplotypes and several thousands of possible pairs of haplotypes in the population.

Using conventional analysis, scientists can sometimes determine whether a given haplotype system is useful for predicting disease status by determining whether trait-affected and non-affected individuals have different haplotypes for a given haplotype system. For example, consider a haplotype system with the possible values GC, GA, CA, CC. If a scientist notes that people who respond well to an anti-cancer drug always have the GC/GC haplotype pair, this scientist has identified the GA, CA and CC haplotypes as risk markers for non-response to the drug. However, this is a relatively simple haplotype system having only four constituents.

Now consider a ten SNP haplotype system where one SNP is the cause of a non-response trait. Referring to FIG. 2, haplotype pair data 200 from four people for an eight haplotype system in a region of the genome relevant to an anti-cancer drug response are shown. Each of these positions illustrates a bi-allelic variant within a larger block of DNA sequence. The nucleotide letters that are the same from person to person are omitted by convention. The letters in column 2 for persons 1 and 3 denote sequence variants 202 (C/C) that causes a non-response to the anti-cancer drug. Response status is shown in the last column.

The four person group of data shown in FIG. 2 may be representative of a larger group of patients. Conventionally, a scientist would first obtain genotypes for each patient at these ten positions and infer haplotypes for these persons as shown in FIG. 2. The scientist would then segregate responders from non-responders and measure whether there were statistically significant differences in haplotype constitution between the two groups. In the example of FIG. 2, persons 2 and 4 would be in the responder group and persons 1 and 3 would be in the non-responder group. Visually comparing the two groups, it is apparent that only position 2 sequences are distinctive between them: non-responders have 2 C's at position 2 and responders have another combination, such as G/G, while the sequence for the other positions is not different between the groups.

Under conventional analysis, however, most genetics researchers do not work at the level of the gene haplotype. About three quarters of researchers who study genetic variation focus on individual SNPs and attempt to draw associations between SNP genotypes and traits. This is called a simple genetics approach, with which there are two problems. First; these studies generally suffer from lack of statistical power to detect associations, a power that is imparted to haplotype studies by systematic genetic forces that have shaped the genetic structure of our modern day population. Second, they are inappropriate for solving complex genetic issues. Because most human traits are complex functions of intergenic (sets of SNPs and ploidy issues) and intragenic (i.e. multiple gene-gene interactions) factors, this is a serious limitation.

On the other hand, about one quarter of geneticists perform their work at higher levels of complexity. These geneticists consider genetic determinants at the level of the haplotype, rather than the SNP, and infer phase using computational methods or directly through biochemical means. Regardless of how phase is determined, haplotype systems are usually defined based on convenience. If a gene has 30 SNPs distributed throughout its sequence, for example, a researcher would likely select a small number of these SNPs as components of a haplotype system for study. This selection process is sometimes based on whether the SNP causes a coding (amino acid) change in the expressed protein, or rather based on the fact that the chosen SNPs cover the gene sequence well from 5' to 3' end. The problem with this approach is that it is somewhat arbitrary and leaves most of the SNPs in the gene untested even though they may be linked to the trait under study.

Most human genes have about 30-50 SNPs. Thus, if variants for such a gene were the cause of the non-response trait, and this variability could be ascribed to one or two SNPs, most of the haplotype systems chosen for study would be worthless for predicting the trait (given the laws of probability). In other words, the constituent haplotypes would not be statistically associated with the trait. (The latter point is slightly complicated by a concept called linkage disequilibrium, but it does not significantly impact the argument presented.) This follows from the observation that there are a large number of possible haplotypes incorporating these SNPs (i.e. $2^{30}$-$2^{50}$, 30 and 50 SNP haplotype systems, respectively) and an even larger number of haplotype pairs in the human population for each gene.

What this means for scientists trying to solve vexing disease and drug-response traits is that there is a large amount of data to sift through in drawing statistical associations between haplotypes, or haplotype pairs, and commercially relevant human traits. For most human genes, the number of haplotype systems that could possibly be invoked to explain variable traits in the human population is far larger than the number that actually explain them. This poses a tremendous statistical barrier for current day genetic research. Furthermore, traits are oftentimes caused by several genes interacting together (i.e. they are "complex"). After identifying optimal haplotype systems within a plurality of genes, the question then becomes how all of these genes work together to cause the trait.

Eye Color. Iris pigmentation is a complex genetic trait that has long interested geneticists and anthropologists but is yet to be completely understood. Eumelanin (brown pigment) is a light absorbing polymer synthesized in specialized lysozomes called melanosomes in a specialized cell type called melanocytes. Within the melanosomes, the tyrosinase (TYR) gene product catalyzes the rate-limiting hydroxylation of tyrosine (to 3,4-dihydroxyphenylanine or DOPA) and oxidation of the resulting product (to DOPAquinone) to form the precursor for eumelanin synthesis. Though centrally important, pigmentation in animals is not simply a Mendelian function of TYR (or any other) gene sequences. In fact, study of the transmission genetics for pigmentation traits in man and various model systems suggests that variable pigmentation is a function of multiple, heritable factors whose interactions appear to be quite complex (Akey et al., 2001; Brauer and Chopra, 1978; Bito et al., 1997; Sturm et al., 2001; Box et al., 1997; Box et al., 2001a). For example, unlike human hair color (Sturm et al., 2001), there appears to be no dominance component for mammalian iris color determination (Braier and Chopra, 1978), and no correlation between skin, hair and iris color within or between individuals of a given population. In contrast, between-population comparisons show good concordance; populations with darker average iris color also tend to exhibit darker average skin tones and hair colors. These observations suggest that the genetic determinants for pigmentation in the various tissues are distinct, and that these determinants have been subject to a common set of systematic forces that have shaped their distribution in the worlds various populations.

At the cellular level, variable iris color in healthy humans is the result of the differential deposition of melanin pigment granules within in a fixed number of stromal melanocytes in the iris (Imesch et al., 1997). The density of granules appears to reach genetically determined levels by early childhood and usually remains constant throughout later life (though, see Bito et al., 1997). Pedigree studies in the mid-seventies suggested iris color variation is a function of two loci; a single locus responsible for de-pigmentation of the iris, not affecting skin or hair, and another pleiotropic gene for reduction of pigment in all tissues (Brues, 1975).

Most of what has been learned about pigmentation has been derived from molecular genetics studies of rare pigmentation defects in man and model systems such as mouse and *Drosophila*. For example, dissection of the oculocutaneous albinism (OCA) trait in humans has shown that most pigmentation defects are due to lesions in one gene (TYR) resulting in their designation as tyrosinase (TYR) negative OCAs (Oetting and King, 1999; Oetting and King, 1993; Oetting and King, 1992; Oetting and King, 1991; see Albinism database at the World Wide Web address cbc.umn.edu/tad/). TYR catalyzes the rate-limiting step of melanin biosynthesis and the degree to which human irises are pigmented correlates well with the amplitude of TYR message levels (Lindsey et al., 2001). Nonetheless, the complexity of OCA phenotypes has illustrated that TYR is not the only gene involved in iris pigmentation (Lee et al., 1994). Though most TYR-negative OCA patients are completely de-pigmented, dark-iris albino mice (C44H), and their human type IB oculocutaneous counterparts exhibit a lack of pigment in all tissues except for the iris (Schmidt and Beermann, 1994). Study of a number of other TYR-positive OCA phenotypes have shown that, in addition to TYR, the oculocutaneous 2 (OCA2) (Durham-Pierre et al., 1994; Durham-Pierre et al., 1996; Gardner et al., 1992; Hamabe et al., 1991), tyrosinase like protein (TYRP1) (Chintamaneni et al., 1991; Abbott et al., 1991; Boissy et al., 1996), melanocortin receptor (MC1R) (Robbins et al., 1993; Smith et al., 1998; Flanagan et al., 2000) and adaptin 3B (AP3B) loci (Ooi et al., 1997), as well as other genes (reviewed by Sturm 2001) are necessary for normal human iris pigmentation. In *Drosophila*, iris pigmentation defects have been ascribed to mutations in over 85 loci contributing to a variety of cellular processes in melanocytes (Ooi et al., 1997; Lloyd et al., 1998) but mouse studies have suggested that about 14 genes preferentially affect pigmentation in vertebrates (reviewed in Strum 2001), and that disparate regions of the TYR and other OCA genes are functionally inequivalent for determining the pigmentation in different tissues.

Though the pigmentation genes are well-documented, until this work, merely a handful of SNP alleles were known to be weakly associated with natural distributions of iris colors in the healthy Caucasian population. The reason for this is that most work attempting to describe natural variation in iris colors has focused on simple genetics approaches, such as single SNP analysis in single genes including the TYR 0, MC1R (Valverde et al., 1997) and ASIP ( ) genes. By developing new complex genetics methodologies and adopting a systematic approach for identifying and modeling genetic features of variable iris color, the problem was analyzed through more of a complex genetics lens than others previously. Nevertheless, most of the results agree with previous literature.

Though the TYR expression product is the rate-limiting step in the catalytic chain leading to the synthesis of eumelanin from tyrosine, previous studies by others have belied the "simplistic" hypothesis that TYR polymorphism is a principle (i.e. penetrant) component underlying normal variation of human pigmentation (Strum). Our study also failed to identify penetrant genetic features of variable iris color in the TYR gene. In addition, the systematic approach for identifying penetrant genetic features independently confirmed that the "red hair" SNP alleles described by Valverde et al., 1995 and Koppula et al., 1997 are indeed associated with iris colors. However, even these simple gene-wise analyses has been extended by the present findings. While there are no SNPs or haplotypes within the TYR gene associated with iris color, TYR alleles are important within a complex genetics context for the inference of iris colors. While the two "red hair" SNPs are indeed associated with natural iris colors (in Irish individuals), they seem to be most strongly associated with Caucasian iris colors within the multilocus context of another coding change in the MC1R gene, and even then, they represent merely one stroke of a larger portrait.

In fact, one important point to be taken from the work described herein is that speaking of variable iris color on the level of individual genes is illogical due to the complexity of the trait. The fact of the matter is, neither TYR nor MC1R, nor for that matter any of the other genes we surveyed, are very important for predicting iris colors on their own. This was indicated by the Bayesian conditional probabilities obtained, which for even the most strongly associated alleles (the penetrant genetic features), were too low for their use as independent classifiers. Since the variance of any complex phenotype is a function of additive, dominance, and epistatic genetic variance (in addition to environmental variance) any good complex genetics classifier must capture each of these three components when making inferences, and the present classifier developed seems to be able to this. The additive component is captured most efficiently through the analysis of multilocus alleles (haplotypes) and the dominance component is captured by expressing individuals as vectors whose components are encodings of multilocus genotypes for each important region.

Though research on pigment mutants has made clear that a small subset of genes is largely responsible for catastrophic pigmentation defects in mice and man, it remains unclear whether or how common SNPs in these genes contribute towards (or are linked to) natural variation in human iris color. A brown-iris locus was localized to an interval containing the MC1R gene (Eiberg and Mohr, 1996), and specific polymorphisms in the MC1R gene have been shown to be associated with red hair and blue iris color in relatively isolated Irish populations (Robbins et al., 1993; Smith et al., 1998; Flanagan et al., 2000; Valverde et al., 1995; Koppula et al., 1997). An ASIP polymorphism was also recently described that may be associated with both brown iris and hair color (Kanetsky et al., 2002). However, the penetrance of each of these alleles is low and in general, they appear to explain but a very small amount of the overall variation in iris colors within the human population (Spritz et al., 1995). Studies such as these for associating genes and traits are gene-centric in that alleles descriptive of variant gene loci are considered as definitive and focal objects.

To date, these methods have not worked well. Because most human traits are complex and genetic wholes are often times greater than the sum of its parts, innovative genomics-based study designs and analytical methods for screening genetic data in-silico are needed that are respectful of genetic complexity (for example, the components of dominance and epistatic genetic variance).

Correspondence Analysis. As a methodology for multidimensional analysis, one might consider using correspondence analysis (COA) to find relationships between haplotype systems in various genes and genetic traits. COA is used to create a spatial representation of a data matrix in such a manner that associations within and between variables can be discerned. COA has been described by various authors, most notably by J. P. Benzecri in his "Correspondence Analysis Handbook" published in 1992 (Statistics: textbooks and monographs, Volume 125, Marcel Dekker, Inc., New York, N.Y.) and by Greenacre, M. J. in his "Theory and application of correspondence analysis" handbook (Academic, London, $1^{st}$ Edition). The methods described by Messrs. Benzecri and Greenacre are applicable to various data having non-negative counts and non-negative continuous measurements. Special considerations and approaches, however, must be made for the analysis of genomics data, and specifically for population genetic data.

COA generally provides the canvas upon which various interpretations can be painted. Various discriminates have been used with COA plots in order to formulate rules for making predictions. For example, in one study of medical relevance, clouds of data were generated for patients receiving a particular therapy, conforming to various attribute values of medical relevance. Patient survival was one of the axes of a plot of variable profiles whose simplex lines were well correlated with this axis. The goal of the study was to enable the classification of a patient based on a COA of various qualitative and quantitative attributes into the cloud of patients to which the individual was most similar so that its survival "value" given the therapy could be learned.

Within the field of molecular biology, several authors have used COA or similar methods for drawing associations between gene expression and cellular state. For example, see Fellenberg, K. et al. *Correspondence analysis applied to microarray data*. PNAS 98(19):10781-10786; and Alter, O. et al., *Singular value decomposition for genome-wide expression data processing and modeling*. PNAS 97(18):10101-10106). These applications required various normalization routines in order to avoid biasing the analysis by considering genes expressed with vastly different amplitudes. Only Alter, Patrick Brown, and David Bostein applied a singular value decomposition method for an analysis of gene expression data. Their method used scaled down dimensions of complex data by decomposition onto principal axes. Their method showed that singular value decomposition provides a useful mathematical framework for processing and modeling genome-wide expression data, which was not directly related to population genetics where parameters are measured differently.

However, gene expression data is inherently different from population genetic data. Gene expression is a measure of amplitude, while population genetic data is a measure of state. Not only does this require different measures for standardization and normalization, but the parameters used to describe population genetic data are different. For example, linkage disequilibrium is a parameter that is only useful for describing relationships between genetic states and cannot be used for gene expression analysis. The ability to analyze encoded genetic states in terms of linkage disequilibrium constants, or other genetic parameters such as allele frequencies, haplotype cladogram positions, etc., is an important feature which differs significantly from previous applications of COA in biology. Gene expression analysis also requires a filtration of insignificant "eigengenes" or rows of genes that do not differ significantly along columns (hybridization or cellular states). Compare this to an application of COA as a modeling tool for genetic factors that are already known from other analytical techniques to be features of phenotype states—that is, row values are already known to not be independently distributed with respect to column values.

Good computational tools for genetic modeling do not currently exist, and it is this need that is addressed by the inventive methods and apparatus described in the present application.

SUMMARY

Methods and apparatus for performing complex genetics classification based on correspondence analysis and linear and quadratic analysis are described herein. In one illustrative example, a method is performed using data from a sample population which includes, for each combination of each diploid haplotype pair of at least two genes and each genetic trait class of a genetic trait, a count of individuals in the sample population associated with both a particular diploid haplotype pair and a particular genetic trait class. A correspondence analysis (COA) is performed on the data from the sample population so as to determine a first plurality of n-dimensional coordinates for each diploid haplotype pair and a second plurality of n-dimensional coordinates for each genetic trait class. A linear or quadratic analysis is then performed based on the first and the second pluralities of n-dimensional coordinates and diploid haplotype pairs of the at least two genes from an individual sample. Advantageously, the method is able to accurately classify the individual sample into one of the genetic trait classes.

BRIEF DESCRIPTION OF THE DRAWINGS

FIG. 6 is a flowchart for describing a method of identifying optimal haplotype systems in various genes prior to performing a correspondence analysis (COA) based method;

MODES FOR CARRYING OUT THE INVENTION

Figures 1, 2:
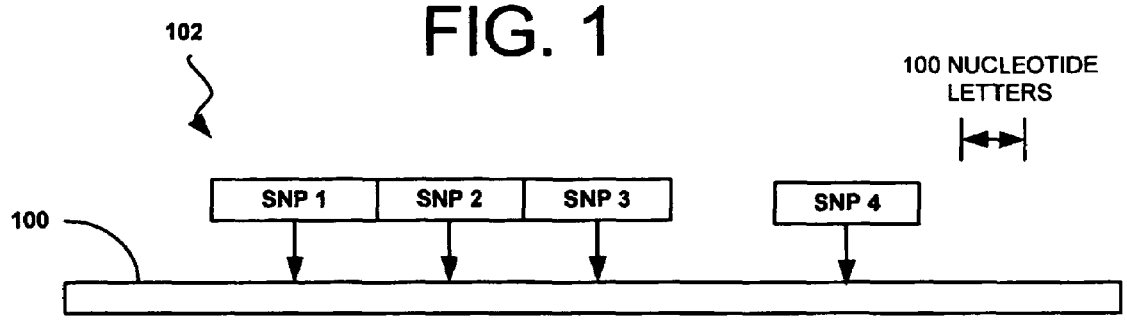
FIG. 1 is an illustration of a gene having a plurality of single nucleotide polymorphisms (SNPs)
FIG. 2 is data which show different haplotype pairs of four different individuals.

How a patient responds to a particular drug, and whether they tend to acquire a particular disease, is largely a function of their genetic background. There is considerable interest in developing genetic solutions for a number of clinically relevant human traits. As described above, however, the problem in the field is that most genetics research is conducted on simple genetics terms, and most of the tools available to researchers are simple genetics tools. Most human traits are complex (involving multiple gene sequences) and the simple genetics analysis of complex genomics data rarely yield classifiers that are sensitive or accurate enough to be used for patient classification. The availability of the human genome map allows complex genetic analysis on a scale never before possible, but in order to realize its potential, researchers must learn how to study genomics data in complex genetics terms. In the near future, physicians may use patient classifiers to determine whether a patient will respond to one type of medication or another, or whether a certain medication will cause side-effects in a patient. Physicians may also be able to predict disease in a patient based solely on their genetic background.

Advantageously, what has been developed is a software-based method which identifies, from high-density SNP arrays, the most informative haplotype systems (or "genetic features") from a plurality of genes, and then performs a correspondence analysis (COA) method, or linear/quadratic analysis method, or a combined approach, for individual/patient classification. The haplotype systems are usually preselected using other algorithms to be of maximum information content; the purpose of the method described herein is to determine how they best fit together to explain the trait. The methods described herein are among the very first complex genetics analytical tools. As such, they enable the production of classifier tests of unprecedented sensitivity, specificity and accuracy. Because only the most sensitive, specific, and accurate testing products will pass Federal Drug Administration (FDA) scrutiny and find a commercial market in the clinic of the future, the tools described herein impart a tremendous commercial advantage.

Eye Color. In particular, a novel population genetics approach has been developed to identify the penetrant "genetic features" of variable human iris pigmentation. Latent genetic features were identified through inference, and both types of features were modeled using a weighted quadratic discrimination method to develop a complex genetics classifier for the accurate inference of iris colors. The results show that out of thousands of possible allele combinations in several human pigmentation genes, only 12 within eight of these genes are necessary for the accurate and sensitive inference of human iris color.

Specimens for re-sequencing were obtained from the Coriell Institute in Camden, N.J., USA. Specimens for SNP scoring were collected from individuals of various ages, sex, hair, iris and skin shades using informed consent guidelines under IRB guidance. Anonymous unique identifiers were assigned to specimens from which DNA was prepared using standard DNA isolation techniques (Qiagen Inc.).

Regarding SNP discovery, vertical resequencing for the various genes was performed by amplifying the proximal promoter, each exon and 3' UTR sequences from a multiethnic panel of 670 individuals. PCR amplification was accomplished using pfu Turbo polymerase according to the manufacture's guidelines (Stratagene). A program was developed to design re-sequencing primers in a manner respectful of homologous sequences in the genome to insure that we did not co-amplify pseudo genes or amplify from within repeats. BLAST searches confirmed the specificity of all primers used. Amplification products were subcloned into the pTOPO (Invitrogen) sequencing vector and 96 insert positive colonies were grown for plasmid DNA isolation. We sequenced with an ABI3700 with PE Applied Biosystems BDT chemistry and we deposited the sequences into a commercial relational database system (iFINCH, Geospiza, Seattle, Wash., USA). PHRED qualified sequences were aligned and analyzed using another developed program for identifying quality-validated discrepancies between sequences.

Regarding genotyping, a first round of PCR was performed on these samples using the high-fidelity DNA polymerase pfu turbo and cognate re-sequencing primers. Representatives of the resulting PCR products were checked on an agarose gel, and firs round PCR product was diluted and then used as template for a second round of PCR incorporating phosphothionated primers. Genotyping was performed for individual DNA specimens using an Orchid single base primer extension protocol and an SNPstream 25K/Ultra High Throughput (UHT) instrument (Orchid Biosystems, Princeton, N.J., USA).

Haplotype frequencies were calculated using the function $p_i=(x_i/n)$, where $x_i$ is the number of times that haplotype i was observed among n number of patients in the group. For contingency analysis, a Pearson's test was used to test the null hypothesis that there was no association between genotypes and eye colors. The associations between specific genotypes and eye colors was also determined and quantified by computing the Adjusted Residuals which was assumed to follow an $N(0, 1)$ distribution as per large sample theory. The 95% confidence intervals were defined by carrying out Multiple Logistic Regression Analysis; it may be noted that estimates of conditional probabilities and their 95% confidence intervals obtained using this approach would be more stable compared to sample proportions, in the sense that the standard error and confidence intervals would be smaller being based on total sample size (n), rather than cell frequencies ($n_{ij}$). Individual haplotypes were inferred from phase unknown genotypes using a computational haplotype reconstruction method (Stephens and Donnelly, 2001).

To identify useful genetic features of variable iris color, an iterative, empirical approach was used to test haplotype alleles of all possible SNP combinations within each gene for the ability to statistically resolve individuals of various trait values. The goal of the screen was to identify whether alleles of a gene were associated with variable iris color and if so, which SNP combinations had alleles most strongly associated with iris color. The predictive phase-known alleles of these SNP combinations were designated as "genetic features" of variable iris color. The SNP combinations themselves were designated as "feature SNP combinations".

For each gene, a list of all possible n-locus SNP combinations was created. The system iteratively:
a) selected an n-locus SNP combination at random;
b) inferred haplotype phase for each individual with respect to this n-SNP combination (if n>2, using the algorithm described by Stephens and Donnelly, 2001);
c) counted the inferred haplotype pairs for the light and dark group;
d) calculated a pair-wise F-statistic, and Fishers Exact test statistic on haplotype pairs ("multilocus genotypes") and a Chi-square adjusted residual statistic on individual haplotypes, in order to determine whether there were significant allele differences between individuals of light (blue+green+hazel irises) and dark (black+brown) iris shade; and
e) repeated the process for the next n-locus SNP combination until all possible combinations within a gene were tested.

The process was repeated for each gene. SNPs or SNP combinations with alleles that were statistically associated with iris color shade (p-value <0.05) were identified as "feature SNP combinations" and/or their alleles with significant adjusted residuals as "genetic features" of variable iris color. To avoid having to test all possible n-SNP combinations (which is computationally intensive), all possible 2-SNP haplotypes were first tested and used these results to guide subsequent tests of higher order SNP combinations. When more than one "genetic feature" was identified within a gene (i.e. in the case of overlapping SNP sets), the set of non-overlapping SNP combinations with the lowest (and significant) p-values within the gene was selected. In the case of multiple non-overlapping features identified within a gene, it was often observed that genotype trait class sample sizes and allelic complexity rendered the alleles of a single (n+m+...)-locus SNP combination less robustly associated with trait value than the component (n-locus, m-locus ...) combinations on their own. In these cases, each of the (n, m, ...) combinations was selected as a "genetic feature" over the single (n+m+...) feature.

To verify and validate the genetic features which were identified, a nested contingency analysis of haplotype cladograms was performed. To do this, it was assumed that both detected and non-detected mutations were potential contributors for phenotypic effects at some point in the evolutionary history of a population, and that these mutations were embedded within the historical structure represented by the haplotype cladogram. Clades were obtained by using PAUP Ver. 4.0b8 software (Outgroup method or Neighbor Joining (NJ) method). Nested cladograms were obtained based on each of the following four methods: (i) Maximum Parsimony, (ii) Neighbor joining, (iii) Maximum Likelihood, and (iv) Bayes Method. In general, the tree for which nested statistical analysis gave the best results was used. Nested contingency analysis was carried out as described by others (Templeton et al., 1997).

General Approaches. General components of software used for the methods include: (1) a database management system that retrieves relevant genetic and phenotype (trait) data for a given problem. The user defines markers to consider (i.e. those within a certain gene) and the trait through a graphical user interface; (2) a process for generating a text file report for visual inspection of each step along the path of problem definition, data collection, and data analysis; (3) a process for selecting a haplotype system for analysis, organizing the data relevant for testing the haplotype system, statistically calculating the haplotype system for analysis, and generating a dynamically updated results file that stores the haplotype system identifier and associated statistical measurements; (4) a process for selecting the combinations of haplotype pairs that are most useful for making classifications of an unknown with reference to the data, which can be considered a "training" set.

Figure 3:
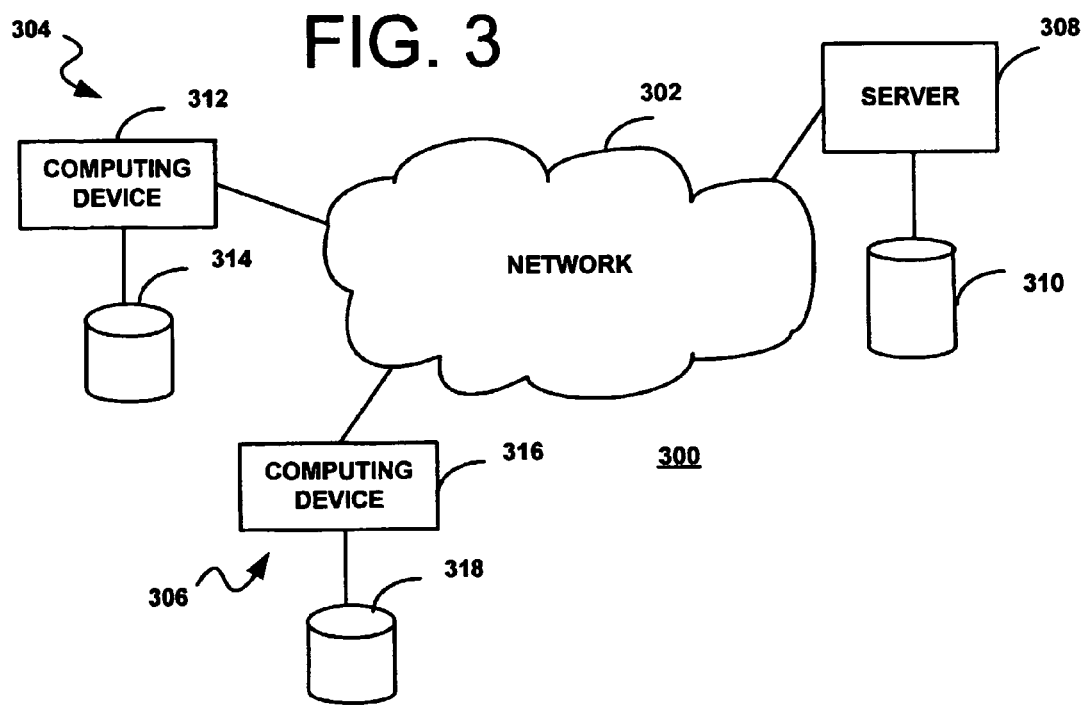
FIG. 3 is an illustration of computer devices in a computer network.

FIG. 3 is a block diagram of a computer system 300 which may embody the present invention. Computer system 300 includes a network 302 and host computers 304 and 306 in network 302. A centrally accessible server 308 and database 310 are also connected in network 302. Each one of host computers 304 and 306 include one or more computing devices and databases. For example, host computer 304 includes a computing device 312 and a database 314, and host computer 306 includes a computing device 316 and a database 318. The computing devices may include any suitable computing device, such as a personal computer (PC), a laptop computer, or a hand-held wireless device. A database, such as database 310, stores gene, genotype, and phenotype data of individuals from one or more sample populations. The inventive software is preferably used in connection with and executed on computing device 312, for example, or server 308 of network 302. Although a preferred computer system is shown and described in relation to FIG. 3, variations are not only possible, but numerous as one skilled in the art would readily understand.

Figure 4:
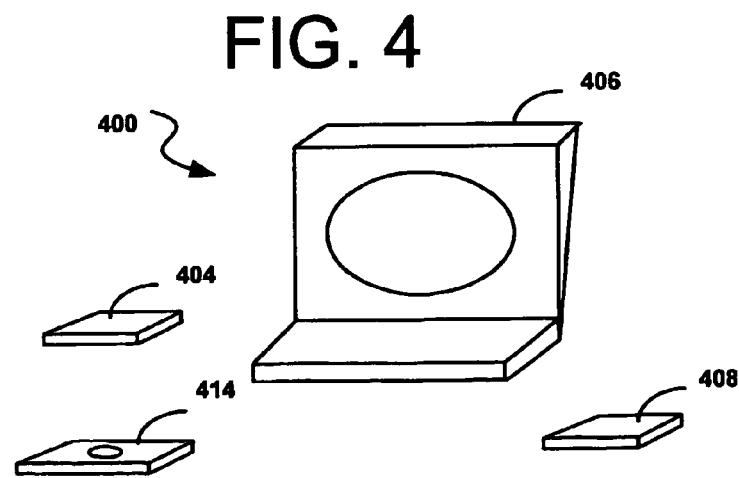
FIG. 4 is an illustration of various computer components which may embody or operate to perform the methods of the present invention.

The methods described herein may be embodied and implemented in connection with FIG. 3 using software components 400 shown in FIG. 4. The software may be embedded in or stored on a disk 414 or memory 404, and executable within a computer 406 or a processor 408. Thus, the inventive features may exist in a computer storage medium which stores computer program instructions which are executable by a computer or computer processor for performing the methods. Such software is preferably used in connection with and executed on computing device 312 or server 308 of network 302 (FIG. 3). Preferably, the system functions within the context of a PC network with a central Sun Enterprise server. The program can be loaded and run on any desktop PC that operates using the Linux or Unix operating system. Other versions could also function in a Windows environment. Alternatively, the software could operate on a publicly accessible server and available for use through a public network such as the Internet.

General reference to FIG. 5 will now be made. What is illustrated is an informatics pipeline system for the efficient and accurate discovery and modeling of genetic features. More particularly, this is a computational pipeline whereby large amounts of value-poor data are input and smaller amounts of value-rich data are produced. More particularly, SNP genotypes and phenotype data are the input data and multivariate solutions relating the various haplotype systems to the trait are the output. The process can be thought of as a sieve or a funnel in that the most informative SNP combinations are culled from many possible combinations and then fit together in the best way possible. Combined with the information about how they fit together to explain the trait, the marker sets constitute a tool that can be used to predict trait values from genotypes.

There are two phases of the process. In the first phase, the pertinent genetic features are identified; in the second phase, the best model for using these genetic features to make genetic predictions is picked. In the first phase, many SNP combinations are tested for the ability of their alleles to resolve between trait classes. In the second phase, the features identified during the first phase are fit together using one or more different mathematical approaches (including a correspondence analysis-based approach). From an input that could include well over 1,000,000 data points and several hundred Megabytes of data (genotypes, clinical tests, etc.), the best possible "solution" present in the data is extracted. The solution could represent one Kilobyte of data or less, depending on the software application used for its presentation and use. The subject of the present invention pertains particularly to a modeling tool utilized in the second phase.

Figure 5:
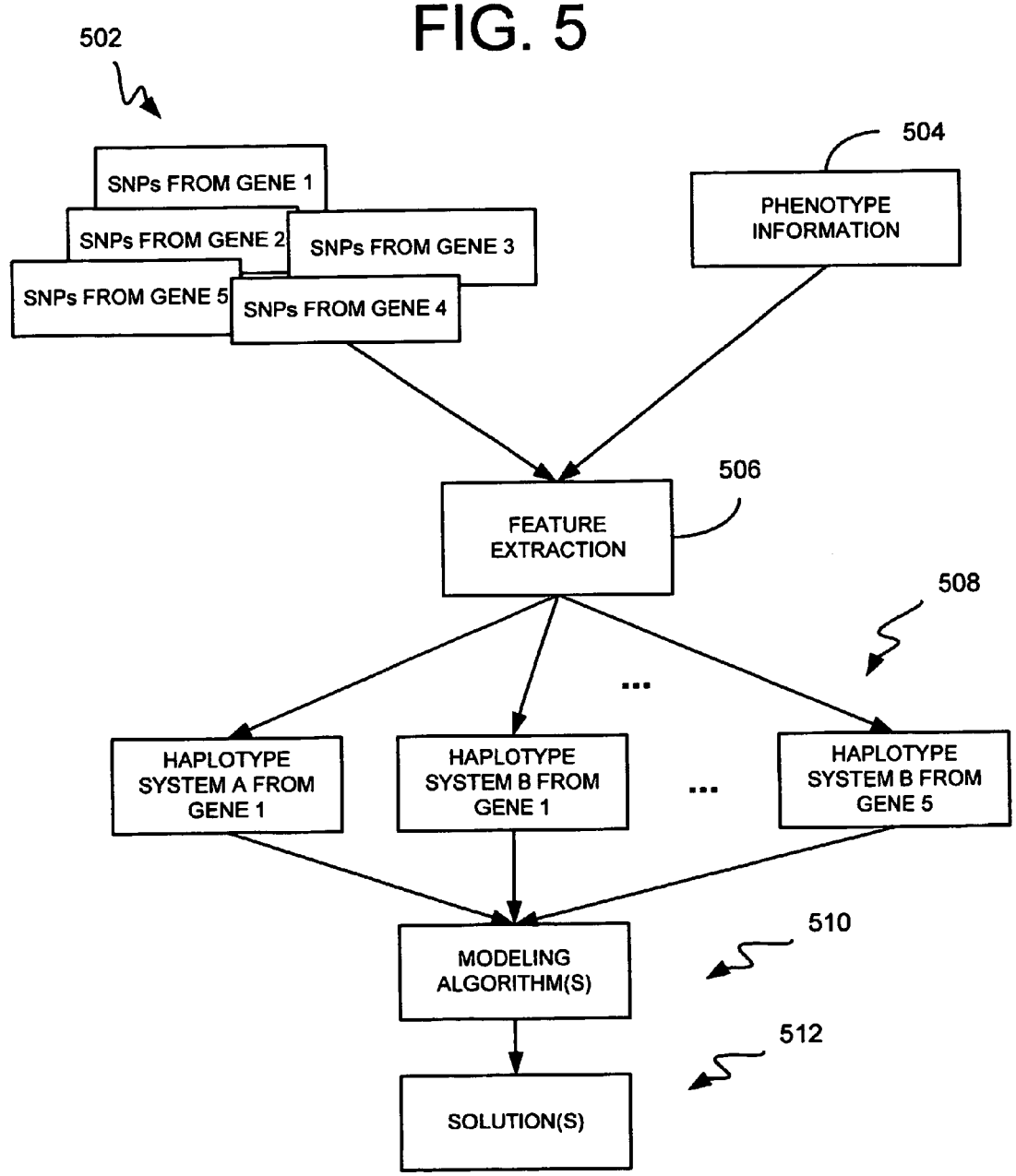
FIG. 5 is a flow diagram for a general overview of the method.

The block diagram in FIG. 5 is an overview of the process for extracting and modeling genetic features for the development of classification tests from SNP genotype or genomics data. Genotype data 502 for a plurality of patients at numerous SNP positions are merged with the patient's phenotype data 504. Data 502 and 504 are input into a feature extraction process 506 to identify significant genetic features 508 (one or more SNP combinations or haplotype systems) that are useful for genetically distinguishing between trait classes. Feature extraction process 506 identifies which genetic features are important or affect the determination of trait class; however, how they fit together (if at all) is determined by one or more statistical modeling algorithms 510 to produce one or more solutions 512. That is, once the features have been identified, the modeling algorithms are executed to weave the features into a complex genetics tale. The inventive techniques described herein relate particularly to one or more statistical modeling algorithms 510, including a correspondence analysis (COA) method, a linear and quadratic analysis method, as well as a combined COA and linear/quadratic analysis method.

FIG. 6 is a flowchart which describes a method of identifying relationships between genetic features and genetic traits. This method is used in connection with software components 400 of FIG. 4 in the systems described in relation to FIG. 3. Beginning at a start block 600, one candidate SNP combination from a plurality of SNP combinations for a gene associated with a particular genetic trait is selected (step 602). Next, haplotype data associated with this candidate SNP combination for a plurality of individuals of a sample population are read (step 604). This haplotype data is grouped into a positive-responding group or a negative-responding group based on whether a predetermined trait criteria for an individual is met (step 606). Alternatively, there may be more than two different trait groups or classes with which the haplotype data is associated. This step is performed by examining phenotype data of each individual. Next, a statistical analysis is performed on the grouped haplotype data to obtain a statistical measurement associated with the candidate SNP combination (step 608). The acts of selecting, reading, grouping, and performing are then repeated as necessary to identify one or more candidate SNP combinations with optimal statistical measurements (step 610). Thus, steps 602-610 are for identifying the "best" haplotype system features in a single gene for a given trait. In one embodiment, steps 602-608 are repeated such that each and every possible SNP combination from all possible SNP combinations is selected and statistically analyzed. Here, when a SNP combination is selected, it is done so in a lexigraphical fashion. In an alternate embodiment, steps 602-608 are repeated such that the SNP combination selection is done in a "directed" fashion to find the optimal solution(s) more quickly and efficiently, without having to test those SNP combinations that are not likely to be optimal.

The identification of optimal features within individual genes is an important first step in developing a genetic "solution" for a trait. However, genetic traits may be caused by several genes interacting together (i.e. they are "complex"). A trait may be caused by certain haplotypes in four different genes, for example. Thus, when such SNP combinations in the single gene are identified, the entire process is repeated for haplotype systems from one or more additional genes (step 612).

Having identified the optimal haplotype systems within each one of the genes, the question then becomes how they work together to cause the trait. Thus, after the optimal haplotype systems for all of the genes are identified, a correspondence analysis (COA) based method is performed (step 614). Alternatively, a linear and quadratic analysis may be performed in step 614. Most preferably, however, a combined COA and linear/quadratic analysis method is performed in step 614.

Consider two groups of genotypes, one from one gene and the other from another gene. Assume that only genotypes for the first gene are relevant to a particular trait. In the case of genetics, genotype values i that do not differ in trait values over genotypes j are of little interest to a complex geneticist. They suggest that there is no relationship in trait values between genotypes i and j. The trait values are independent and not a function of the two genotype groups, although either genotype group on its own may show a relationship with certain trait values. Therefore, all that exists to be learned about the trait can be had from a knowledge of i (or j) on its own. The trait value will be as large as i is large (or as large as j is large). Though, this may be useful for some simple genetic applications, most genetic traits are functions of multiple genes having epistatic interactions (which means that their effect of one genotype on the trait is dependent on the other genotype).

The concept of genetic "epistasis" recognizes that for most traits, there is a relationship between genotypes i and j in predicting trait value. Finding genotypes i and j is one problem, but once they are found, determining how or if they work together to determine the trait is another problem. Indeed, the dependence of row and column attributes towards a trait value {k(i,j)} is precisely what is desired to learn so that a trait can be predicted When a trait is determined by multiple genetic factors, this interdependence is crucial for its understanding.

While it is generally easy to identify individual genes and genotypes that are related to a particular trait, it is more difficult to identify the complex genetics of a trait—how the genes work together in trait determination. This is the problem solved by the present method which is based on a correspondence analysis, a linear/quadratic discriminant analysis, as well as their combined use. Using these methods to produce a complex genetic model shows how individual "genetic features" of a trait function together to determine the trait (if at all). The ability to model genetic data in complex terms is crucial for the development of classifiers from gene associations—they help gain an understanding how the puzzle pieces fit together to form a picture. The present techniques are well-suited for "complex" genetic analysis, which is defined as the study of traits with multiple genetic determinants.

Correspondence Analysis (COA) for Trait Classification. The first modeling technique to be described is based on correspondence analysis (COA) which helps to determine whether and how genetic features (such as haplotype systems) combine to explain a complex genetic trait. A COA-based method is a powerful multivariate graphical procedure to study the association between variables (i.e. instances of genetic features) and attributes (i.e. trait values), and can be considered a scaling method linked to principal component analysis and cononical correlation analysis.

In the present COA technique, values and attributes are represented within a contingency table of i rows (the observed haplotype pairs for each haplotype system) and j columns (trait classes). From this table, what is constructed is an orthogonal system of axes through Principal Components, where row and column attributes are jointly displayed in a k dimensional space. In this space, the distance between the row (i) attributes and the distance between the column (j) attributes is preserved, where k=min{i−1, j−1}. Two row points that are close to each other in the k dimensional space indicate that the two rows have similar profiles (conditional distributions) across the columns. Similarly, two column points close to one another in the space indicates that the column attributes share similar profiles (conditional distributions) down the rows. Proximity between row and column points indicate that particular row-column (haplotype pair, eye color) combinations occur more frequently than would be expected based on the assumption of independence, and thereby indicate a strong association between the row (haplotype pairs) and column (eye color) attributes.

A typical output from the COA includes the 'best' two- (or three-) dimensional representation of the data with the coordinates of the plotted points (i, row points; j, column points) along with a measure (called the inertia) of the amount of information retained in each dimension. Multidimensional space is represented with multiple two-dimensional plots. The display coordinates $x_i^{(g)}$, g (genotype or haplotype system) (i=1, 2, . . . $n_g$) and eye color $x_j^{(c)}$ (j=1, 2, . . . $n_c$) are obtained by minimizing $$L = \sum_{i}^{n_g} \sum_{j}^{n_e} f_{ij}[x_i^{(g)} - x_j^{(c)}]^2 \quad (1)$$

under the constraints that the mean coordinates are zero with variance=1, and where $f_{ij}$ is greater than or equal to zero. It may be noted that the cost function (1) relates genotypes (haplotypes) to trait values in a more direct way than the classification tree methods such as CART. Benzecri described how the relative contribution of row and column variables towards the final result (k) could be explained in a geographical sense using the concepts of mass and inertia. Consider a two-way table of data:

TABLE 1

| Row/Column | j | j' | Marginal Column |
|---|---|---|---|
| I | k(i, j) | k(i, j') | k(i) |
| i' | k(i', j) | k(i', j') | k(i') |
| Marginal Row | k(j) | k(j') | k |

Each row in Table 1 represents a specific variable, each column another variable and each cell of the table represents an instance of data dependent on the specific row and column. Each row and column is described as a profile of all cells in the row or column. For example, row i is described as { . . . k(i,j), k(i,j'), . . . } and column j is described as { . . . k(i,j), k(i',j), . . . }.

Let k(i) and k(j) are marginal row marginal column from i-th and j-th column respectively. In other words: k(i)=Σ{k(i,j)|j for all J} is the total of the row i over all columns j in J. k(j)=Σ{k(i,j)|i for all I} is the total of the column j over all rows i in I. k is the grand total of the table over all rows i and all rows j. In other words; k=Σ{k(i,j)|i for all I; j for all J}.

The relative contribution of a row towards the grand total is called its mass. The mass of i-th row is $f_i$=k(i)/k and the mass of j-th column is $f_j$=k(j)/k. That is, the mass of any individual cell towards the marginal row or column values is simply the quotient of the cell value by the marginal value. The division of the relative contribution of row by cell values is an important method for determining whether and how the row and column variables are related to one another.

However, before these determinations can be made, the relative contribution of groups of rows by groups of columns must be understood. For this, Benzecri introduced the concept of a profile. The profile represents the relative contribution of a row, column or cell towards the marginal value. In COA, the element i of I is not represented by its row in the table but by its marginal value times its profile, which is the sequence deduced from the original row by dividing each term k(i,j) by the total k(i). The profile of i-th row is therefore $f_j^i=\{f_j^i|j \in J\}$ and the profile of j-th column is $f_i^j=\{f_i^j|i \in I\}$, where $f_j^i$=k(i,j)/k(i), is the proportion of j in the i-th row and similarly, $f_i^j$=k(i,j)/k(j) is the proportion of i in j-th column.

To illustrate why the profile is more useful than the discrete set of values representing a row or column, suppose we had the following table:

TABLE 2

| | n | v | a | a' | L | | p |
|---|---|---|---|---|---|---|---|
| i' | 80 | 30 | 25 | 15 | 60 | 55 | 265 = k(I') |
| i" | 160 | 60 | 50 | 30 | 120 | 110 | 530 = k(I") |

In the above Table 2, it is clear that the two rows are proportional to one another. The second is obtained from the first by multiplying all of the numbers by 2. It shows that each row is distinct from the other but profiles are same. That is, Profile (i')=$f_j^{i'}$={80/265, 30/265, 25/265, 15/265, 60/265, 55/265} and Profile (i")=$f_j^{i''}$={160/530, 60/530, 50/530, 30/530, 120/530, 110/530} are same. These two rows are identical. By representing the rows as profiles multiplied by the marginal row value, we obtain more information about the row than by representing it by its discrete values. In this case, we can recognize a common dependence between row and column values for these two rows. For example, when the column value is v, the row value will be 30 if the row is i' and 60 if the row value is i". Using profiles, however, shows that when the column value is v, the row value will be 0.113 of the total for that row, whether the row is i' or i".

The case where row profiles are the same implies that there exists no particular affinity between values i and j, and gives no scope for an analysis. When all rows of the table have the same profile, the profile can be shown to be equivalent to the profile $f_j$ and $f_i$ of the marginal row and columns, respectively. In other words, all that can be learned from the table is found in the marginal rows and columns—no specific difference within rows or columns exist and therefore no particular relationship between rows and columns exits; the data is best described using an agglomerate of the table values. In fact, in genetics as well as other disciplines, we desire to discover differences of profiles, and the attractive or repulsive interactions between the rows i and columns j.

In the space of the profiles over J, or I, each row or column is represented (called Spatial Representation) by a vector of profile to which is assigned a mass. The set of profiles for a group of rows or columns, weighted by mass, constitute a cloud when plotted in n-dimensional space. An element of the cloud is represented by a pair formed by a row profile and the mass of this row and is represented by N(I)={($f_j^i$, $f^i$)|i∈I}. Each element can be plotted in a multidimensional space. Since the profile components equal 1, when an n-dimensional profile is plotted in n-dimensional space, the subspace within this space that contains the coordinates is n−1.

Figure 7A:
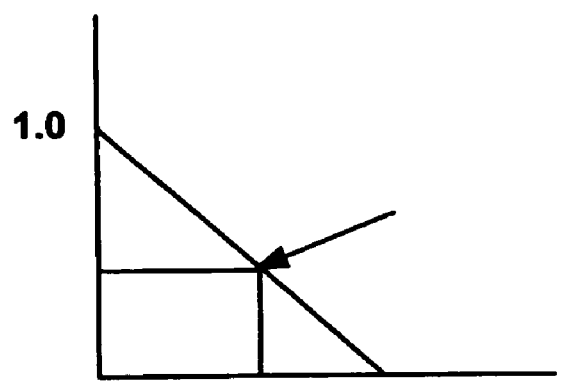
FIGS. 7A-7C are graphs which illustrate concepts relating to COA.
Figure 7B:
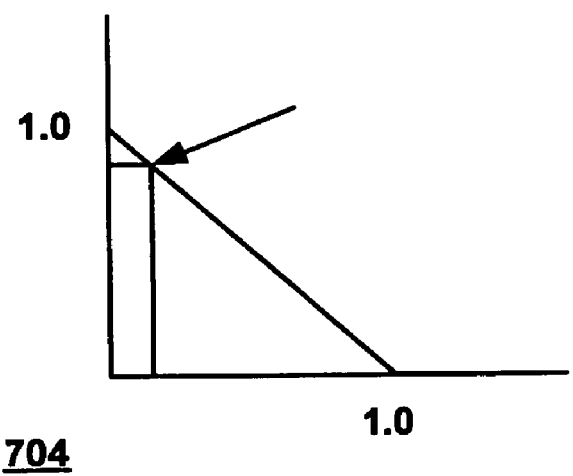
Figure 7C:
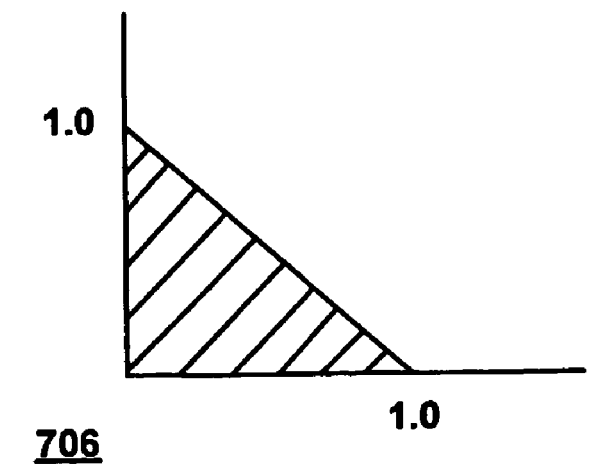

To illustrate, reference is now made to FIGS. 7A-7C. As an example, if the profiles are 0.5 and 0.5 they are plotted in the two dimensional space where the arrow points in a graph 702 of FIG. 7A. If another profile has the components 0.2, 0.8, they are plotted where the arrow points in a graph 704 of FIG. 7B. In fact, for any two combinations that add up to 1, the subspace within which the profile must exist is within the triangular area noted by the shaded area in a graph 706 of FIG. 7C. In these graphs, the position on the diagonal line upon which the profile coordinates meet is a one-dimensional feature. Thus, two 2-dimensional objects can be projected into 1-dimension (i.e. on a line). The same applies to plots of dimensions greater than two (2).

Simplifying the data in this manner is a reduction of dimensionality, or a means to produce a convenient system of profiles. In this way, the dimensionality of data can be simplified, for a more tractable representation and analysis. When the dimensionality of the data is large, typically COA projects the data onto the first 2 or 3 dimensions. Whether or not this is a good projection is determined by comparing the amount of variance the projection explains relative to the chi-square statistic for the entire contingency table. When rows are related to columns (a situation we desire to learn), the condensation of the data into lower order space tends to allow for an explanation of most of the variability in the original table as measured with the chi-square statistic.

The center of gravity of a system of points with masses assigned to them (their actual positive or non-zero values) constitute a spatial generalization of the mean of these points. Similarly, the center of gravity, or the moment, of a set of profiles with masses assigned to them (as defined above) is a spatial generalization of the concept of a mean of profiles. The center of gravity of points $f_i^j$, to each of which has been assigned a mass $f_i$, is like the mean of the cloud of points N(I). Where in the space the points lie is determined by their profiles, but the mean for each point $f_j^i$, allows us to identify a center of gravity for the cloud. For example, we have just seen how a two-dimensional profile can be represented as a point on a line. After we define the simplex for the space of profiles (in our example, a line), we can plot instances of profiles and observe that the most frequently found instances are closest to value $p_j$, which in probabilistic sense, is the "center of gravity of the simplex for the space of profiles. If counts for profiles along a line are shown in a histogram along that line, where the magnitude of the counts is projected perpendicular to the line, a bell curve would form and the point on the line corresponding to the apex of this curve would be center of gravity value $p_j$.

While calculating the mean of a cloud of points in a more complex spatial representation, the center of gravity is computed in a likewise manner. The profiles determine the space within which the points lie (the cloud) but the mass allows us to calculate the center of gravity for the points, based on the importance of a given profile towards the table results. For a plane, this is done by calculating the center of gravity of points projected upon the x-axis, and then calculating the center of gravity of points projected upon the y-axis. In the example of a two by two table, assume that one j variable among the subset J begets a large k(i,j) for certain i values within the subset I. Profiles for rows of these certain I rows will register in the simplex as distant from the mean. The distance from the mean can be used to infer individuality or conformity to a mean. The center of gravity of a shape constructed of points of equal mass is a simple matter of geometry. When the points are of unequal mass, the center of gravity shifts towards points of greater mass. This point is referred to more correctly as a "Barycenter" G, to distinguish it from the geometrical center of gravity (the center of gravity of the shape). For a cloud of points N(I) and N(J) in dimensional space greater than 3, we can no longer visualize the center of gravity, or the Barycenter of the cloud because the ambient space has too many dimensions. However, these points are computed in the same way as described above, using the weighted means of the coordinates, axis by axis. The Barycenter is the spatial mean, with each point playing a role proportional to its mass.

Thus, COA proceeds from a representation of numerous instances of data in a table in terms of row and column profiles, spatially representing these profiles in a manner that reduces their dimensionality (their simplex profile), and identifying the center of gravity, or more correctly, the Barycenter for the simplex using the masses of the various profiles used in its construction. Thus, we have effectively made a spatial generalization of the data such that the interrelationships between variables part of the contingency table can be visually appreciated. Such a representation enables one to understand how to classify new points relative to the parameters that are described by the cloud, and this is one of the subjects of the present invention.

Before this can be appreciated, one must know something about the variance of the points about the cloud. The cloud of points in N(I) is more or less dispersed around its center of gravity. The dispersion of the cloud around this center of gravity, as a whole, can be calculated from the distances between points and the center of gravity. Rather than measure the deviation between two points by measuring the distance between them, the square of this distance is measured (for reasons beyond the scope of this discussion). In COA, the dispersion of the points in a cloud about a particular point (such as the center of gravity) is called inertia. Points of a cloud are projected on one of the axes, and for each axis, the inertia of the cloud N is defined as:

$$I_G(N) = \Sigma\{m_i d^2(G, M_i) | i=1, \ldots, n\}$$

where G is the center of gravity, $M_i$ is a particular point in the cloud, and $d^2(G, M_i)$ is the sum of square of deviation between the $M_i$ and G. The inertia around any particular point P can be shown to be determined by:

$$I_P(N) = I_G(N) + m_{tot} d^2(G, P)$$

Where $m_{tot}$ is the total mass of N, that is, $m_1 + m_2 + \ldots + m_n$. The total variance of the cloud N is:

$$Var_{tot}(N) = I_G(N)/m_{tot} = \Sigma\{m_i d^2(G, M_i) | i=1, \ldots, n\}/m_{tot}$$

The total variance is the weighted mean of the dispersion of points in the cloud about the center of gravity for the cloud. In other words, it is a measure of the overall dispersion of the points in the cloud about their center of gravity. The standard deviation is the square root of this value.

COA shows how the clouds N(I) and N(J) are represented around their respective centers of gravity $f_J$ and $f_I$. The distributional distance between two rows in the space of profiles over J is given by the formula:

$$d^2(f_j^i, f_j^{i'}) = \Sigma\{(1/f_j)(f_j^i - f_j^{i'})^2 | j \in J\}$$

Similarly, the distance between the columns j and j' (in the space of profile over I) is $$d^2(f_i^j, f_i^{j'}) = \Sigma\{(1/f_i)(f_i^j - f_i^{j'})^2 | i \in I\}$$

The distributional distance is also referred to as $X^2$-distance in statistics and is given by $$\chi^2\text{-distance}=\Sigma\{(1/k(j))(k_{ij}/k(i)-k(j)/k)^2(k(i)|j\epsilon J\}.$$

The total inertia (trace) is the sum of the inertia of the various points of the cloud with respect to the center of gravity:

$$\text{Trace}=\Sigma\{\{(1/(f_if_j))(f_{ij}-f_if_j)^2\}|i\epsilon I \text{ and } j\epsilon J\}.$$

Absolute contribution of the cell (i,j) to the trace is $$CA(i,j)=(1/(f_if_j))(f_{ij}-f_if_j)^2=f_if_j(d^{ij}-1)^2$$

wherein $d^{ij}=f_{ij}/f_if_j$ is the density of the distribution $f_{IJ}$ with respect to the distribution of the product $f_if_j$. The relative contribution of the cell (i,j) to the trace is $$CR(i,j)=CA(i,j)/\text{trace}.$$

The cloud is represented in a Euclidian space, and a system of lines are constructed that are mutually perpendicular and pass through the center of gravity. These are called the principal axes of inertia, or factorial axes. The clouds N(I) and N(J) can be projected upon these axes simultaneously, and the points of the cloud defined in this manner are called factors. In this regard, COA is related to principal components analysis.

Factors $F_k(i)$ and $G_k(j)$ obtained from their respective clouds can be written by formulae, each symmetric (Barycentric symmetric principle) with respect to other, as $$F_k(i)=(1/\lambda_k)\Sigma\{f_j^iG_k(j)|j\epsilon J\}$$

$$G_k(j)=(1/\lambda_k)\Sigma\{f_i^jF_k(i)|i\epsilon I\}$$

where $\lambda_k$ is the standard deviation of factor $F_k$ (or $G_k$). We have variance explained by $F_k$ (k-th principal inertia), $\lambda_k^2\Sigma\{f_iF_k(i)^{2|i\epsilon I}\}$. The principal inertia of factor k, $p_k=\lambda_k^2/\Sigma(\lambda_k^2)$ for k=1, 2, ..., NF=Min(r−1,c−1), shows the variability explained by the k-th factor. The Shannon entropy of a data set, $0\leq e=(-1/\ln(NF))\Sigma_k p_k \ln(p_k)\leq 1$, measures the complexity of the data from the distribution of the overall expression due to different row points (and column points), where e=0 corresponds to ordered and redundant data set in which over all expression is explained by a single factor, and e=1 corresponds to a disordered and random dataset in which overall expression is equally expressed by all factors.

The quality of representation of a point over first two dimensions can be obtained to know how well the points explain most of the variability on these two axes. The distribution of each component to each factor (absolute contribution) and the distribution of variability over a factor by the components represents the relative contribution. We can obtain individual variability (inertia) of row and column points.

Basically what COA accomplishes is a geometric and simultaneous representation of row and column profiles in a lower dimensional subspace of the data table. The end to which this is useful is dependent on the extent to which the representation allows us to understand how the variables of the table are related to one another. If row profiles and column profiles are the same, then knowing one obviates the need to know the other. If row and column profiles are distinct, but functions of one another, then we discover the differences of row and column profiles so that the attractive and repulsive interactions between the variables can be learned.

Detailed COA Algorithm. A more detailed algorithm for the COA method is described below:

Step 1. (a) Read a raw data matrix, $K=(k_{ij})$ of order NI×NJ, where rows represents genotypes and columns represents corresponding eye colors, where I={1, 2, ..., NI} and J={1, 2, ..., NJ}. (b) Compute marginal column, $k(i)=\Sigma\{k(ij)|j\epsilon J\}$, marginal row, $k(j)=\Sigma\{k(i,j)|i\epsilon I\}$ and grand total of $k=\Sigma\{k(i,j)|j\epsilon I \text{ and } j\epsilon J\}$. (c) Compute the mass of the i-th row and mass of j-th column respectively by $f_i=k(i)/k$ and $f_j=k(j)/k$. (d) Compute the i-th row and j-th column profile of correspondence matrix, $(f_{ij})=(k_{ij}/k)$ respectively by $f^i_j=\{f^i_j=k_{ij}/k(i)|j\epsilon J\}$ and $f^j_i=\{f^j_i=k_{ij}/k(j)|i\epsilon I\}$. (e) Compute the difference of observed and expected frequencies of (ij)th cell, $d_{ij}=(f_{ij}-f_if_j)$.

Step 2. Determine principal inertias (eigenvalues). (a) Let the matrix be defined as $S=(s_{ij})$, where $s_{ij}=(f_{ij}-f_if_j)/(\sqrt{f_if_j})$ is submitted to singular value decomposition (SVD), i.e., the product of three matrices: $S=UAV^T$, where A is a diagonal matrix, and its diagonal elements are referred to as the singular values of S. These singular values are sorted from largest to smallest and denoted by $\lambda_k$. The eigenvalues are obtained as square of singular values and denoted by $\lambda_k^2$. Total inertia= $\Sigma(\lambda_k^2)$. (b) Compute the principal inertia of factor k, $p_k=\lambda_k^2/\Sigma(\lambda_k^2)$ for k=1, 2, ..., NF=Min(r−1, c−1). (c) Shannon entropy of a data set, $e=(-1/\ln(NF))\Sigma p_k \ln(p_k)$.

Step 3. Determine principal coordinates. (a) Compute the i-th row coordinate of k-th factor is given by $F_k(i)=\lambda_k u_{ik}/\sqrt{f_i}$ for k=1, 2, ..., NF and similarly, compute the j-th column coordinate of k-th factor is given by $G_k(j)=\lambda_k v_{jk}/\sqrt{f_j}$, for κ=1, 2, ..., NF=Min(r−1, c−1). (b) Standard (std) co-ordinates: The std coordinates of i-th row of k-th factor is $u_{ik}/\sqrt{f_i}$ and the std coordinates of j-th column of k-th factor is $v_{jk}/\sqrt{f_j}$ for k=1, 2, ..., NF=Min(r−1, c−1).

Step 4. (a) Quality of i-th row point over all NF dimensions is $QLT(i)=\Sigma_k F_k(i))^2/\Sigma_k (F_k(i))^2$. (b) Mass of i-th row point is $f_i=k(i)/k$. (c) Inertia due to i-th row element: $INR(i)=f_i\Sigma_k F_k(i)^2/\Sigma_i f_i\Sigma_k(F_k(i))^2$. Similarly, quality, mass, and inertia for column points can be determined respectively as follows: (d) Quality of j-th column point over all NF dimensions is $QLT(j)=\Sigma_k G_k(j))^2/\Sigma_k (G_k(j))^2$, (e) Mass of j-th column point is $f_j=k(j)/k$, and (f) Inertia due to j-th column element= $INR(j)=f_j\Sigma_k F_k(j)^2/\Sigma_j f_j\Sigma k(F_k(j))^2$.

Step 5. (a) Relative Contribution of the factor k to the inertia of i-th row point is given as follows: $COR_k(i)=(F_k(i))^2/\Sigma_k(F_k(i))^2$. (b) Absolute Contribution of the i-th row point to inertia of the k-th factor $(\lambda_\kappa)$ is $CTA_\kappa(i)=f_i(F_\kappa(i))^2$ and relative contribution of the i-th row point to k-axis is $CTR_k(i)=f_i(F_k(i))^2/\lambda_k^2$. Similarly, for column points, j: (c) Relative Contribution of the factor k to the inertia of j-th column point is given as follows, $COR_k(j)=(G_k(j))^2/\Sigma_k(G_k(j))^2$. (d) Absolute Contribution of the j-th column point to inertia of the k-th factor $(\lambda_k)$ is $CTA_k(j)=f_j(G_k(j))^2$, and (e) Relative contribution of the j-th column point to k-axis is $CTR_k(j)=f_j(G_k(j))^2/\lambda_k^2$.

Step 6. Compute factor scores: The i-th row score of κ-th factor is $s_\kappa(i)=\Sigma G_k(j)k_{ij}$ and the j-th column score of κ-th factor is $c_\kappa(j)=\Sigma F_k(i)k_{ij}$.

Step 7. Discrimination/classification of eye colors: either standard co-ordinates of first two dimensions of row and column points or Z-scores of first two factors will be plotted on a plane in order to classify the eye color which are associated with genotypes by using hyper plane technique.

Figure 8:
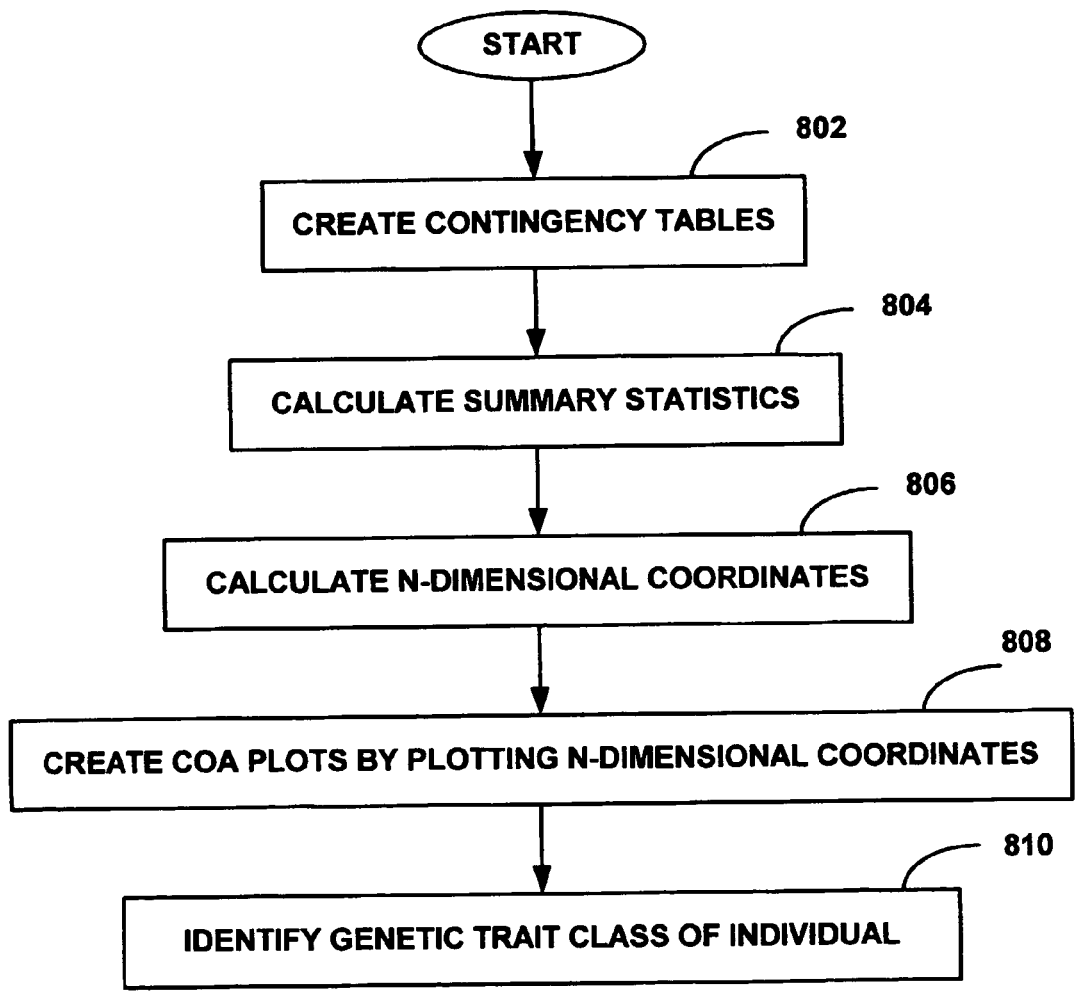
FIG. 8 is a flowchart for describing a method of complex genetics classification based on COA.

FIG. 8 is a flowchart which generally describes the algorithm for complex genetics classification based on a correspondence analysis (COA). For each gene of a plurality of genes, a contingency table is created (step 802). Each table has rows corresponding to a plurality of diploid haplotype pairs in the gene and columns corresponding to a plurality of genetic trait classes (e.g. different eye colors) for a genetic trait (e.g. eye color). Each data cell of the table contains a count of individuals in a sample population that associated with both the corresponding diploid haplotype pair and the corresponding genetic trait class. Each table may or may not be constructed as a formal visual table; but at the very least a data table having appropriate associations is stored (temporarily or permanently) in computer memory. Next, for each table created, summary statistics are calculated (step 804) for each diploid haplotype pair and for each genetic trait class. The summary statistics include moment and inertia values. Next, for each table, a plurality of n-dimensional coordinates for each diploid haplotype pair and for each genetic trait class are calculated (step 806). These calculations are based on the corresponding table data and summary statistics which were previously calculated.

Next, one or more correspondence analysis plots may be generated, by plotting the first and the second pluralities of n-dimensional coordinates determined for each table (step 808). If such "scatter plots" are created, diploid haploid pair points of an individual can be suitably analyzed in connection with these plots. A genetic trait class associated with the individual can be identified based on this analysis (step 810). As an alternative to (or in addition to) plotting these coordinates, a linear or quadratic analysis using the n-dimensional coordinates may be performed (described later below).

If plotting is performed, the method may use both standard and raw coordinates for plotting the coordinates of the first two factors of row and column points on a plane in order to understand the best way of associating genotypes with traits. The algorithm may select the best plot of the two by measuring the average distance from the centroid to each data point within a particular class. The plot with the largest average distance is chosen. This is important because, with certain data, the dispersion obtained using raw coordinates is too large, which distorts the classification process and leads to classification error. In other cases, the dispersion is too low, which imparts minimal power to discriminate between samples and/or traits, rendering COA useless. Oftentimes, when the dispersion is either too great or too small for one of the methods, it is more suitable using the other and by choosing between the two. This feature imparts a substantial advantage for interpreting a COA plot.

A framework for determining whether a COA is worth computing may also provided. Because a COA computation may take an hour or more using state-of-the-art computational hardware, in order for the method to be useful as a screening tool for the identification of epistatic components of genetic variance, uninformative plots must be eliminated before they are constructed and analyzed. In the present embodiment, the "Shannon entropy" of a dataset is used as a trigger to decide whether a plot is worth constructing and analyzing. The "Shannon entropy" is defined as:

$$0 \le d = -1/\log(NF) \sum_{k=1}^{NF} p_k \log(p_k) \le 1$$

which measures the complexity of the data from a distribution over all rows and columns. When a contingency (or correspondence) table captures most of the variance of columns with plots of row coordinates, it is deemed to be a good plot since it allows for the inference of column state from row values. In this case, the Shannon entropy is low. When the Shannon entropy is high, it suggests that the row and column coordinates are randomly distributed with respect to one another (i.e. there is no association between row or genotype values and column or phenotype states). The greater the distance between row coordinates, the lower the entropy and the stronger the rows are positively associated with column states when the row and column coordinates are along a line in the same direction from the centroid of the plot (when they are in opposite directions from the centroid, they are negatively associated, which also implies value). When the dataset is redundant (i.e. degenerate), the complexity is low and little can be learned about column states from row values. In this case, the COA plot will show as a bunching of points around the centroid, and since little can be learned about positive or negative association, the plot is not worth constructing. The algorithm recognizes these low-value plots before they are constructed, saving days worth of compute time when analyzing complex population genetics projects.

Thus, the COA proceeds from a representation of numerous instances of data in a table in terms of row and column profiles, spatially representing these profiles in a manner that reduces their dimensionality (their simplex profile), and identifying the center of gravity, or more correctly, the Barycenter for the simplex using the masses of the various profiles used in its construction. Thus, a spatial generalization of the data may be made such that the interrelationships between variables part of the contingency table can be visually appreciated. Though COA as previously described does not provide for it, such a representation enables one to understand how to classify new points relative to the parameters that are described by the cloud. The present embodiment of COA to population genetics research is advantageous in that it provides a mathematical framework for using a COA plot of genetic features to develop a classifier. Once a plot has been obtained that displays genetic feature values (haplotype pairs for n-loci) and trait values, geometric approaches for classification of individuals (row values) with respect to phenotype states (column values) are used.

The first COA classification technique is to form pericentric rings around each column coordinate. An individual is classified into the column state whose rings contain the largest number of coordinates representing his row values in the ring and we impose a penalty for the number of row coordinates not within the ring based on their distance from the centroid of the ring. The radius of the circles are successively increased until discrimination is accomplished. The quality of the discrimination is assessed using rectangular confidence intervals around the centroid. In a good plot (where the Shannon entropy is low, or where the chi-square statistic of the original contingency table is high), an individual can be classified within the first few cycles of ring expansion. In a bad plot, even the largest rings do not lead to discrimination because rings for disparate column (phenotype) states contain a similar number of row coordinates within the positive and negative subspaces. This technique is described later in detail. A variation of this technique calculates the average Euclidian distance between row coordinates and column coordinates and classifies the individual (row) into the state (column) for which the average distance is lowest.

Another variation of the COA classification technique calculates the center of gravity of a geometrical shape constructed by connecting the row coordinates characteristic of an individual, and calculating the Euclidian distance between this center of gravity and each of the column (phenotype) coordinates. Classification is accomplished by selecting the column coordinate for which this Euclidian distance is minimum. If the center of gravity does not fall within the confidence rectangle of a trait coordinate, the individual can either be classified as inconclusive or into the trait class that the center of gravity is closest to. Alternatively, the classification is the trait class into which most of the other points in that region of the graph are classified. In a good plot, using good genetic features, each of these techniques would produce the same result. This technique is outlined, step-by-step later in the description.

The above classification methods are useful for ascribing associations between genes and traits. Epistasis is the interaction between loci in determining a trait, and epistatic traits are those in which there exists a complex relationship between genotype and phenotype. Most human traits are subject to some level of epistasis, which the present method is particularly adept to detect. The COA plot may suggest epistasis in cases where specific multilocus genotype combinations are strongly associated to one trait coordinate, but where other multilocus genotype combinations for the same genes are strongly associated to other traits in the plot. If the method accepts SNP or haplotype data during contingency table formation, it is especially powerful for detecting epistatic associations between variants and traits that other association study designs have no power to detect (i.e. so-called "purely" epistatic traits). If the method is used as described herein, where features of the trait are entered into the contingency table, it is useful in identifying the epistatic component of traits that are not purely epistatic (which it is believed represents most human traits). In other words, if one feature value positively or negatively influences the effect of another on trait value with respect to making a specific classification, the classification techniques described above will accommodate this relationship during construction of the COA classifier plot. Whether purely epistatic or not, the detection of epistasis requires that genotype combinations be entered into the rows, in addition to the individual genotypes. This increases the dimensionality of the analysis significantly. By discerning the inter-relationships between gene variant combinations and the trait value with COA analysis, it is possible to formulate classification rules sensitive to epistasis.

The present method may also accommodate gene X environment interactions, if environmental variables are included in the original contingency table. The ability to formulate classification rules sensitive to gene x gene interactions and gene x environment interactions (which distinguish common Complex Genetic traits from rare Mendelian genetic traits) is particularly unique. The COA application described here represents a novel complex genetic analysis tool for large-scale, case-control and population-based study of the relationship between polymorphisms and human traits.

Ancillary Applications of the Methods. The method can be expanded to accomplish feature extraction. By testing all possible markers within all possible genes (in rows) against trait values (in combinations), markers and marker combinations that are related to the traits can be learned. In this case, rather than provide as input qualified genetic features, all genetic values can be input where COA discerns which are associated and which are not.

Example Using COA. An example of using COA analysis in population genetics research for classification of human eye color using pigmentation haplotype combinations will now be described. Prior to COA analysis, five (5) haplotype systems whose constituent haplotypes were predictive of human eye color were identified. These identified haplotype systems are TYR2LOC920, OCA3LOC920, OCA3LOC109, TYRP3L105 and MCR3LOC105. Though haplotypes for each haplotype system were statistically associated with various eye colors, it was found that none of these haplotype systems on their own could comprise an accurate classifier. Therefore, a correspondence analysis was performed.

A contingency table for this analysis is shown in Table 3. This table was part of a correspondence analysis of human eye color that incorporated the above five haplotype systems; for simplicity only the TYRP3LOC105 system is shown. More particularly, the counts of individuals of the various diploid haplotype pairs (rows) for each of the eye color classes (columns) are shown.

TABLE 3

Contingency table for the TYRP3LOC105 haplotype system.

Correspondence Analysis Contingency Table
For Eye Colors

| TYRP3LOC105 | Blue | Green | Hazel | Brown | Sum |
|---|---|---|---|---|---|
| g(1,1):GGA/GGA | 5 | 0 | 7 | 20 | 32 |
| g(1,2):GGA/GGT | 5 | 2 | 6 | 8 | 21 |
| g(1,3):GGA/GTT | 28 | 5 | 15 | 14 | 62 |
| g(1,4):GGA/TGA | 0 | 0 | 0 | 2 | 2 |
| g(1,5):GGA/TTT | 0 | 0 | 3 | 0 | 3 |
| g(1,6):GGT/GTT | 0 | 1 | 0 | 0 | 1 |
| g(1,7:GGT/TGA | 1 | 1 | 1 | 1 | 4 |
| g(1,8):GTA/GTT | 0 | 1 | 0 | 0 | 1 |
| g(1,9):GTT/GTT | 8 | 7 | 18 | 16 | 69 |
| g(1,10):GTT/TGA | 1 | 1 | 1 | 3 | 6 |
| g(1,11):GTT/TTT | 4 | 2 | 1 | 1 | 8 |
| Total (n) | 72 | 20 | 52 | 65 | 209 |

Summary statistics and coordinates derived from this contingency table are shown below in Tables 4 and 5, respectively.

TABLE 4

Summary statistics for the row points used for the COA of human eye color with five haplotype systems (only TYRP3LOC105 haplotype system shown here).
Summary Statistics for the Row Points

| Genotype | Mass | Inertia |
|---|---|---|
| g(1,1) | 0.0306 | 0.065 |
| g(1,2) | 0.0201 | 0.0044 |
| g(1,3) | 0.0593 | 0.0144 |
| g(1,4) | 0.0019 | 0.0173 |
| g(1,5) | 0.0029 | 0.0354 |
| g(1,6) | 0.001 | 0.037 |
| g(1,7) | 0.0038 | 0.0045 |
| g(1,8) | 0.001 | 0.037 |
| g(1,9) | 0.066 | 0.0086 |
| g(1,10) | 0.0057 | 0.0067 |
| g(1,11) | 0.0077 | 0.0154 |

TABLE 5

Coordinate dimensions for genotypes derived from the contingency table and summary statistics for use in plotting the graphical representation of genotypes relative to trait values for the eye color problem.
Correspondence Analysis of TYRP3LOC105 genotypes and eye color

| Genotype | Dimension 1 | Dimension 2 | Dimension 3 |
|---|---|---|---|
| g(1,1):GGA/GGA | 0.9251 | 0.064 | 0.0108 |
| g(1,2):GGA/GGT | 0.4738 | 0.0008 | 0.5254 |
| g(1,3):GGA/GTT | 0.5966 | 0.0738 | 0.3295 |
| g(1,4):GGA/TGA | 0.995 | 0.0026 | 0.0024 |
| g(1,5):GGA/TTT | 0.1039 | 0.2681 | 0.628 |
| g(1,6):GGT/GTT | 0.0644 | 0.8639 | 0.0717 |
| g(1,7):GGT/TGA | 0.072 | 0.7229 | 0.2051 |
| g(1,8):GTA/GTT | 0.0644 | 0.8639 | 0.0717 |
| g(1,9):GTT/GTT | 0.9341 | 0.0057 | 0.0602 |
| g(1,10):GTT/TGA | 0.5562 | 0.3778 | 0.066 |
| g(1,11):GTT/TTT | 0.3919 | 0.5184 | 0.0896 |

Having used COA to define the n-dimensional coordinates for the genotypes, the same routine is performed to define the n-dimensional coordinates for the trait value classes (in this case eye color) (Tables 6 and 7).

TABLE 6

Summary statistics for the column points (eye colors) used in the Correspondence analysis of human eye color with the 5 haplotype systems.
Summary Statistics for the Column Points

| Trait | Mass | Inertia |
| --- | --- | --- |
| Blue | 0.3445 | 0.1717 |
| Green | 0.0957 | 0.2582 |
| Hazel | 0.2488 | 0.1651 |
| Brown | 0.311 | 0.405 |

TABLE 7

Coordinate dimensions for trait values derived from the contingency table and summary statistics for use in plotting the graphical representation of genotypes relative to trait values for the eye color problem.
Column Coordinates for Trait Values

| Trait | Dimension 1 | Dimension 2 | Dimension 3 |
| --- | --- | --- | --- |
| Blue | 0.2732 | −0.0552 | −0.2103 |
| Green | 0.2964 | 0.7415 | 0.1495 |
| Hazel | 0.2127 | −0.2335 | 0.2501 |
| Brown | −0.5639 | 0.0198 | −0.0132 |

Figure 9:
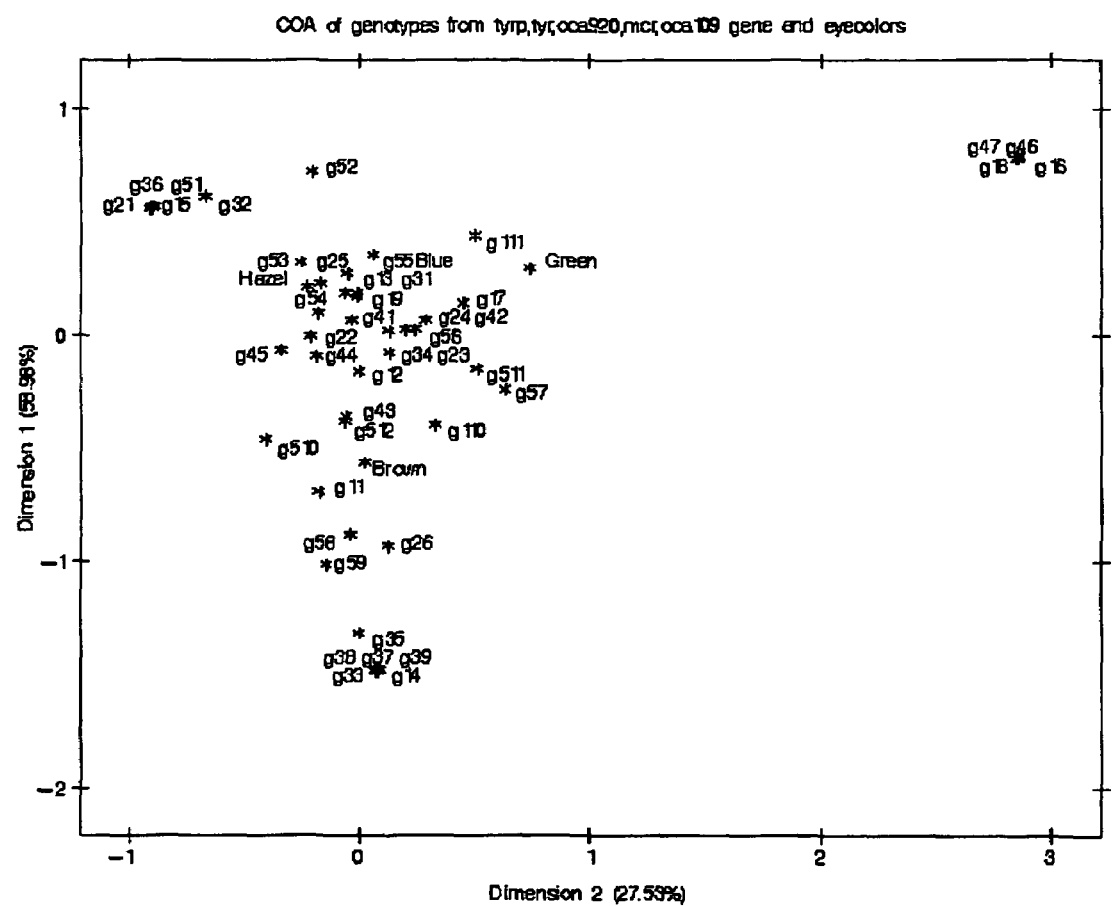
FIG. 9 is a first correspondence analysis scatter plot which shows associations between specific genotypes and eye colors in dimensions 1 and 2 of the analysis.
Figure 10:
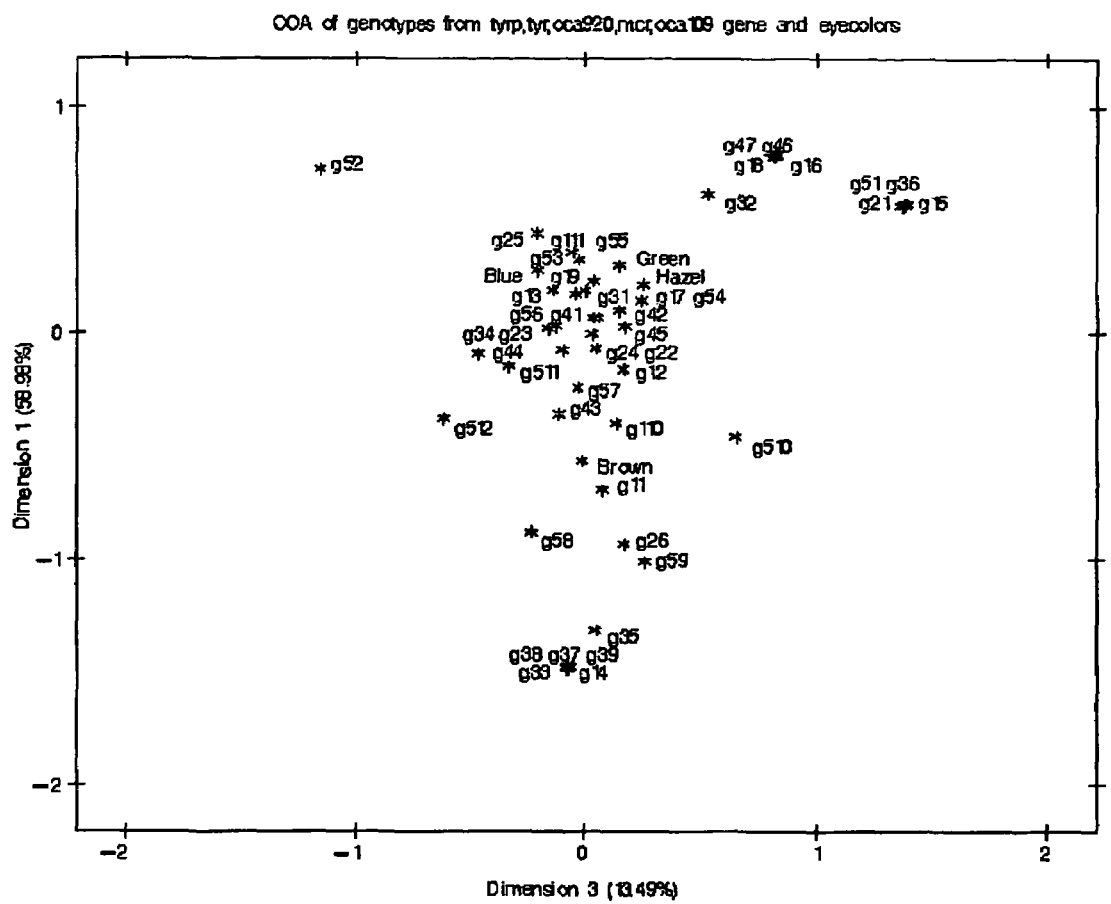
FIG. 10 is a second correspondence analysis scatter plot which shows associations between the specific genotypes and eye colors in dimensions 1 and 3 of the analysis.
Figure 11:
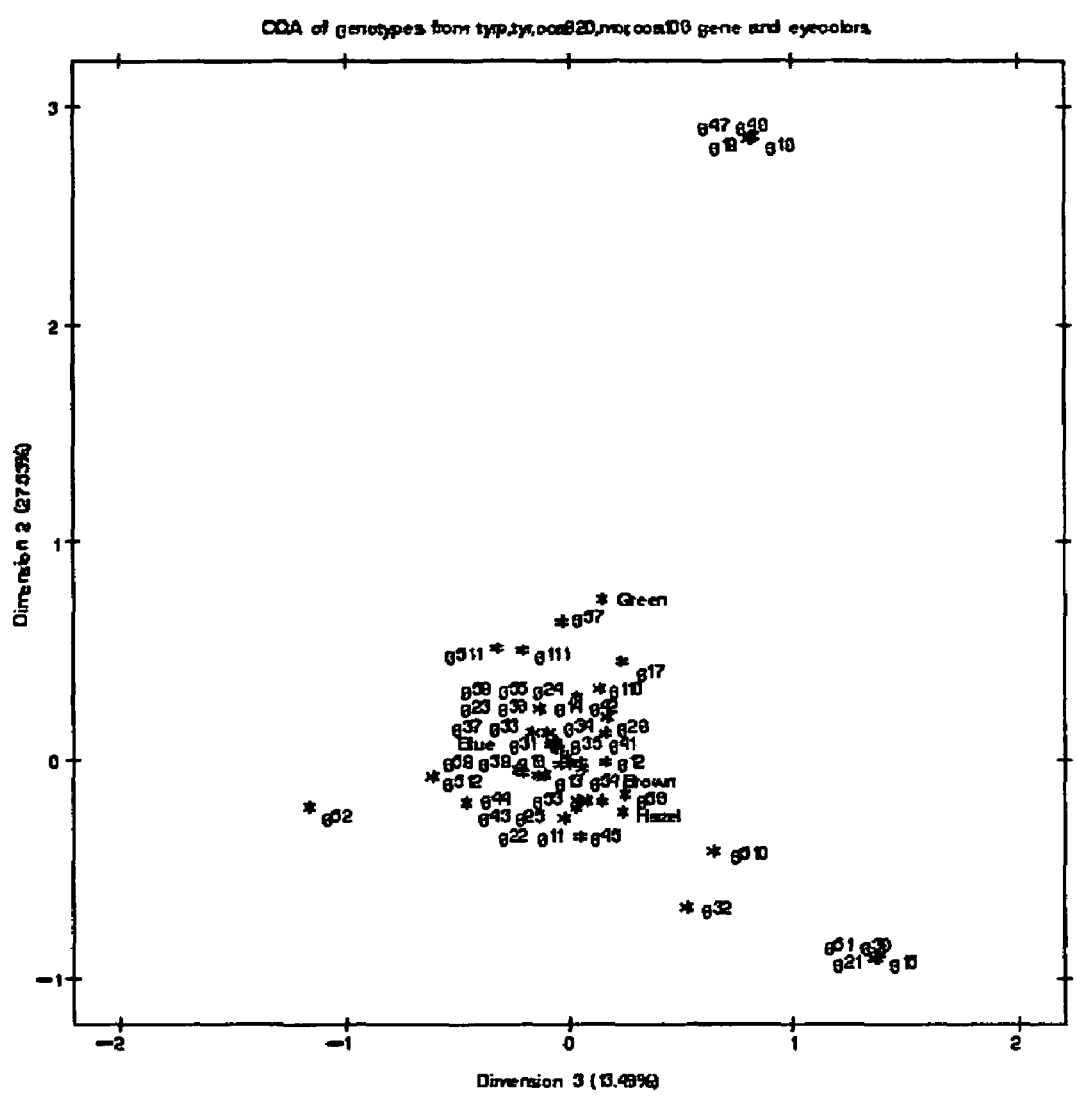
FIG. 11 is a third correspondence analysis scatter plot which shows associations between the specific genotypes and eye colors in dimensions 2 and 3 of the analysis.

Having identified n-dimensional coordinates for the genotypes and trait values, the program then plots these coordinates in the n-dimensional feature space. The relationship between genotypes and eye color are illustrated in 2-dimensional graphs 900, 1000, and 1100 shown in FIGS. 9-11, respectively. This is done such that the distances between genotypes and eye colors are preserved and such that genotypes which primarily distinguish certain types of eye colors are spatially close (and in a positive relation) to those colors. Thus, the graphical display of simultaneous representation of genotypes and eye colors reveals that the distance of a given genotype from the centroid towards a color shows the strength of its association with that eye color in the same direction and vice versa. COA does not depend on model assumptions, and the projection of z scores aims to find the major trends in the data ignoring minor fluctuations. Moreover, the COA method has the capacity to analyze mixed data of non-negative counts and continuous measurements.

To classify an individual as belonging to one or another trait class, the coordinates of their genotypes are identified in the n-dimensional feature space (not shown due to the difficulty of visually representing a 3-dimensional object on a 2-dimensional surface). The program typically operates within the confines of a 3-dimensional space. Connecting genotype coordinates within a 3-dimensional space forms a rhombozoidal shape with a moment or center of gravity. The Euclidian distance between this moment and the coordinates for the eye color classes is linearly proportional to the probability that the individual is a member of each class. Therefore, a classification decision can be made based on these distances; for example, if the moment is closest to the coordinates for green eye color, then we classify the individual as belonging to the green eye color class. Furthermore, an important set of rules must be used to resolve cases where the distances between moment and more than one trait value is similar (defined arbitrarily, but defined as being within 5% distance of one another). If this is the case, when the two competing trait values are juxtaposed along a continuous scale (such as blue and green eye color along the continuum of eye colors from light to dark), then the classification is most accurately identified as a trait class that combines these two trait values (such as Light eye color).

Adopting this approach and these rules, it was found that individuals could be classified into the proper eye color class, or shade of eye color class, 97% of the time using these five haplotype systems as genetic features. Eye color has been a complex genetic trait that has vexed geneticists for decades. This "solution" was the very first solution for human eye color. The successful application of Correspondence Analysis for solving this trait illustrates the utility of this approach for solving complex human traits with genomic data sets.

Thus, a software-based method for performing complex genetics classification based on correspondence analysis has been described. For each gene of a plurality of genes, a table is created having rows corresponding to a plurality of diploid haplotype pairs in the gene and columns corresponding to a plurality of genetic trait classes. Each data cell in each table contains the number of individuals in a sample population that exhibit the corresponding diploid haplotype pair and fall into the corresponding genetic trait class. For each table created for each gene, a first plurality of n-dimensional coordinates for each diploid haplotype pair and a second plurality of n-dimensional coordinates for each genetic trait class are determined based on data in the table and summary statistics (e.g. moments and inertias). Correspondence analysis plots may be created by plotting the first and the second pluralities of n-dimensional coordinates determined for each table. The plot is a visual aid. Alternatively, the visual plotting step can be skipped, and a linear or quadratic analysis may be employed (described below) directly with use of the first and the second n-dimensional coordinates determined from the correspondence analysis. Advantageously, a genetic trait class of an individual can be identified through the analysis of diploid haploid pair points of the individual.

Linear and Quadratic Classifier Construction Tool for Multivariate Trait Classification using Multi-Locus Geneotypes. A software-based method for generating linear and quadratic classifiers incorporating multiple genetic attributes is now described. This method has certain strengths and weaknesses over pure correspondence analysis, which is better for situations where the trait is subject to genetic dominance. Because of its simplicity, this method is superior to correspondence analysis when the trait is subjected to additive affects but not to genetic dominance. The better approach, as will be described below, is to combine both the COA and the linear/quadratic analysis.

The problem of classifying a given individual as a member of one of several populations or groups to which that particular individual can possibly belong is interest to many types of scientists (i.e. statisticians, geneticists, anthropologists, taxonomists, psychologists etc.). There are mainly three approaches in the classification analysis, namely, (1) parametric, (2) semi-parametric, and (3) non-parametric and their robust (Balakrishnan-Ambagaspitiya, 1991) versions. In each approach, many contributions have been made by various authors (e.g. McLachlan, 1992). Though linear and quadratic classification procedures have been well documented in the literature, few algorithms have been generated for their implementation as software tools within the field of complex genetics. It is believed that the present technique is the first such algorithm developed in this field. What is used is a parametric multivariate linear classification (Fisher, 1936) and Quadratic classification (Anderson, 1958; Srivastava et al., 1979) with modifications for genomics data (Spilman et al., 1976; Smouse et al., 1976). What is unique is the use of the method with population genetics data—where SNP, haplotype and multilocus genotype alleles, and/or their COA coordinates are used as variables for the linear/quadratic discriminate procedure.

Under the assumption that the samples have taken from multivariate normal distributions with different mean vectors with common variance covariance matrix, linear classification procedure introduced by Fisher (1936), Rao (1947, 1948a, 1948b), or Smith (1947) can be applied. However, if the populations have different variance covariance matrices, quadratic classification should be used.

For linear classification, the pooled within-population variance-covariance matrix can be computed from $$S = \Sigma^{p}_{i=1} \Sigma^{N_i}_{j=1} (Y_{ij} - m_i)(Y_{ij} - m_i)' / \Sigma(N_i - 1) \qquad (1)$$

Where $Y_{ij}$ is the vector of character measurements for the j'th individual in the i'th trait value, and, $m_i$ and $N_i$ are the vector of means and sample size for the i'th trait value. The generalized distance of the ij'th individual form the mean of the k'th trait value can be computed from $$D^2_{ij,k} = (Y_{ij} - m_k)' S^{-1} (Y_{ij} - m_k) \text{ for } k \neq i \qquad (2)$$

The vector $Y_{ij}$ is used to calculate $m_k$, the mean of its own eye color. To avoid circularity caused by this, Smouse (1976) used a correction when comparing an individual with the mean of its own eye color:

$$D^2_{ij,i} = (N_i/(N_i-1))^2 (Y_{ij} - m_i)' S^{-1} (Y_{ij} - m_i) \qquad (3)$$

The usual procedure is to allocate the ij'th individual to that trait value for which (2)/(3) is minimum.

Human Eye Color (Genotype Data). The problem is predicting an individual's eye color based on multilocus genotypes data. Results from a study of 300 individuals are presented. Within population variance-covariance matrices were computed, and randomly selected individuals were classified based on their genetic distance from the mean of each eye color class (see Table 8 below). If one considers Blue, Green, and Hazel as Light and Brown and Brown 3 as Dark(i.e. a dark brown), then the classifier is found to be, on average, 82.2% accurate in classifying an individual into the proper shade of eye color. It so happens that, for this trait and these markers, the quadratic classifier is more appropriate.

TABLE 8

Linear classification matrix for randomly selected individuals of varying eye color. The frequency with which individuals of a given eye color class are classified as belonging to a given eye color class is shown.

|  | Blue | Green | Hazel | Brown3 | Brown |
|---|---|---|---|---|---|
| Blue | 0.4457 | 0.22 | 0.1566 | 0.012 | 0.1566 |
| Green | 0.1818 | 0.5909 | 0.1363 | 0 | 0.09 |
| Hazel | 0.2372 | 0.2203 | 0.40677 | 0.0169 | 0.118 |
| Brown3 | 0.0602 | 0.048 | 0.024 | 0.795 | 0.072 |
| Brown | 0.1176 | 0.098 | 0.137 | 0.176 | 0.4705 |

For quadratic classification, the quadratic discriminant score for the i'th trait value is $$D^2_{ij,k} = \ln|S_k| + (Y_{ij} - m_k)' S^{-1}_k (Y_{ij} - m_k)$$
$$\text{for } k = 1, 2, \ldots, g \text{ (eye colors)} \qquad (4)$$

Classification is then simply the allocation of the ij'th individual to that trait value for which (4) is minimum.

Human Eye Color (Haplotype Data). For the human eye color example, using the five (5) optimal haplotype systems, it is found that the quadratic classifier results in a more accurate classification matrix than the linear classifier (Table 9). Because the samples have different means and unequal variances, the quadratic classification procedure is more appropriate for the data considered above. Not only are blue-eyed individuals classified as blue-eyed, green-eyed individuals classified as green-eyed, etc., more accurately using the quadratic approach, but the classification of individuals into the proper shade of eye color (Light or Dark) is also more accurate (Table 10). When accuracy is measured in terms of an individual of a given eye color shade properly classified into that eye color shade, the quadratic method produced a 93% accuracy rate (Table 11).

TABLE 9

Quadratic classification matrix for randomly selected individuals of varying eye color. The frequency with which individuals of a given eye color class are classified as belonging to that a given eye color class is shown.

|  | Blue | Green | Hazel | Brown3 | brown |
|---|---|---|---|---|---|
| Blue | 0.54321 | 0.04819 | 0.3253 | 0.0241 | 0.06 |
| Green | 0.045 | 0.9545 | 0 | 0 | 0 |
| Hazel | 0.1525 | 0.0508 | 0.7118 | 0.0169 | 0.0677 |
| Brown3 | 0.036 | 0 | 0.1325 | 0.807 | 0.024 |
| Brown | 0.098 | 0.0588 | 0.2156 | 0.196 | 0.4313 |

TABLE 10

Accuracy of the quadratic classification method in terms of eye color shade for the various eye colors. The eye color shade is shown in Columns 2 and 3.
The eye colors are shown in each row.

| Eye Color | Light | Dark |
|---|---|---|
| Blue | 91.60% | 8.40% |
| Green | 100% | 0% |
| Hazel | 91.50% | 8.50% |
| Brown | 15.70% | 84.30% |
| Brown3 | 3.60% | 96.40% |

TABLE 11

Overall accuracy of the quadratic classification method for the two eye color shades.

| Shade | Correct | Incorrect |
|---|---|---|
| Light | 94.40% | 5.60% |
| Dark | 90.40% | 9.60% |
| Total | 93% | 7% |

Combined COA and Linear/Quadratic Technique. What is now described is the integration of Linear/Quadratic Techniques with the COA technique. It will be noted from the results presented below that the integration of the two techniques produced superior results than the use of either on their own (described above).

The transmission of iris color from parents to offspring is complex and has been poorly understood. To determine whether and how common polymorphisms are associated with natural distributions of iris colors, novel analytics and data resources have been applied for a candidate gene survey of eight of the most important human pigmentation genes. Five hundred sixty-five Caucasians of varying iris colors were genotyped for 338 SNP loci in these genes. Using a novel heuristic approach, phase-known alleles were identified for the DCT gene (1 combination, 3 SNPs), MC1R-A gene (1 combination, 3 SNPs), OCA2 gene (5 combinations, 17 SNPs) and TYRP1 gene (1 combination, 2 SNPs) to be strongly associated with variable iris pigmentation. Because their association with iris colors was strong enough to be detected using pair-wise F-statistics or Fishers Exact test statistics [avg. p(association)<0.01], these alleles were termed "penetrant genetic features" of variable iris color. Haplotype alleles of SNP combinations within the other 4 pigmentation genes were not statistically associated with variable iris colors in Caucasians but showed unusual frequency differences among racial groups of darker and lighter average iris color shades. It was thus inferred that these alleles may contribute towards iris color variance through epistasis, and they have been termed "latent genetic features" of variable iris color.

To model these features for the construction of a classifier for variable iris color, correspondence analysis methods have been used to derive a novel Quadratic discriminate algorithm. Using only the penetrant genetic features, what was generated was a complex classifier model that generalized to an additional group of 225 Caucasians with 99% accuracy for the inference of iris color shade, but only 91% accuracy for the inference of actual iris colors. Using both penetrant and latent genetic features, what was generated was a complex classifier model that generalized to the same group with 99% accuracy for the inference of iris color shade, and 97% accuracy for the inference of actual iris colors. The results showed that the identification of predictive markers for complex traits, such as iris pigmentation, is best accomplished in a manner that is respectful of intergenic complexity and that accurate classification models incorporating genetic features are best developed in a manner that is respectful of intragenic complexity.

To use the haplotype alleles for the inference of iris colors, a software program for using a parametric, multivariate Quadratic classification technique with modifications for genomics data was created. A Monte Carlo simulation study was used to generate the distribution and summary statistics for the probabilities of correct and incorrect classifications using the linear/quadratic classification method. A program was developed to use a random number generator to select 200 individuals on the basis of observed allele frequencies from both light and dark iris color shade groups, and used these individuals to calculate a multivariate linear classification probability matrix. This experiment was repeated 10,000 times to get the summary statistics of Classification and misclassification rates and their Confidence Intervals.

Results. The public databases (NCBI: Unigene, dbSNP, LocusLink) were resequenced and mined and the literature was reviewed to identify 181 candidate SNP loci in 8 pigmentation genes (an average of 23 candidate SNPs per gene) (see column 2, Table 12 below). Genotypes were scored for each of these candidate SNP loci in a group of 335 Caucasians of self-reported iris color (97 brown, 117 blue, 36 green, 85 hazel) as well as in 230 additional individuals of varying racial backgrounds (100 Caucasian, 100 African American and 30 Asian individuals). A software system was developed to screen the phase known alleles of all possible n-SNP combinations for association with trait value (if any, where n=[1, 2, . . . x] and x=the number of SNP loci). The screen was carried out in case control format, encoding iris color shade as light or dark (where light blue, green or hazel and dark=black and brown). In all, we screened alleles of 411 n-locus SNP combinations and of these, alleles of 8 optimally discriminate combinations in 4 of the genes were identified as strongly associated with variable Caucasian iris color (column 5, Table 12). The combinations were unequally distributed among the OCA2 (n=5), TYRP (n=1), DCT (n=1) and MC1R (n=1) genes.

TABLE 12

Genetic Feature Extraction Results for Human Eye Color.

| Gene | Candidate SNPs[1] | Σ(n-SNP) Tested[3] | # of Genetic Features[4] | Selected Haplotype Feature Name, Feature IDs[5] | P-Value |
|---|---|---|---|---|---|
| AP3B1 | 6 | 1 | 0 | None | — |
| ASIP | 18 | 14 | 0 | None | — |
| DCT | 20 | 15 | 1 | DCT-B, (702\|650\|675) | <0.001 |
| MC1R | 16 | 8 | 1 | MC1R-A, (217438\|217439\|217441) | Insig*. |
| OCA2 | 36 | 189 | 5 | OCA2-A, (217458\|886894\|886895\|886896) | <0.001 |
|  |  |  |  | OCA2-B, (217452\|712052\|886994) | <0.001 |
|  |  |  |  | OCA2-C, (712057\|712058\|712060\|712064) | 0.001 |
|  |  |  |  | OAC2-D, (712054\|712056\|886892) | 0.002 |
|  |  |  |  | OCA2-E, (217455\|712061\|886892) | 0.003 |
| SILV | 14 | 105 | 0 | None | — |
| TYR | 46 | 13 | 0 | None | — |
| TYRP1 | 28 | 66 | 1 | TYRP-A, (886938\|886943) | <0.020 |
| TOTAL | 181 | 411 | 8 | 25 SNPs in 4 genes |  |

Footnotes for Table 12:
[1]Total number of SNPs in each gene tested for allelic association with iris color.
[2]Total number of n-locus SNP combinations whose haploid alleles were tested for association with iris color using the genetic feature extraction algorithm described in the text. The number was dependent on the number of validated SNPs found from the total in column 2 (data not shown), and the results from lower order (i.e. 1, 2-locus combination) screens as described in the methods.
[3]Number of non-overlapping SNP combinations, alleles of which were identified as genetic features for variable iris color as described in the text.
[4]Name and SNP composition for each of the identified genetic features.
[5]F-statistic P-value for the Haplotype Feature allele sequence composition between individuals of light and dark iris shade as described in the text.
*one haplotype for this combination was found to be strongly associated with iris color shade, but the other observed haplotypes were not significant.

Because their association with iris colors was strong enough to be detected with simple genetics approaches, haplotype alleles of these SNP combinations were termed "penetrant genetic features" of, and the SNP combinations themselves "penetrant feature SNP combinations" of variable iris color. No penetrant genetic features or penetrant SNP combinations were identified in the TYR, SILV, ASIP or AP3B1 genes (Column 5, Table 12). The 8 penetrant genetic features were comprised of 25 SNPs, of an average minor allele frequency 0.21 (range 0.07-0.47). Four of these were coding changes, seventeen (17) were located in introns and four (4) were silent changes (see column 6, Table 13 below). Ten of the SNPs were identified from resequencing (not present in the NCBI:dbSNP database or the literature) though alleles of two of these (217439 and 217441, Table 13) turned out to have been identified before as related to human pigmentation in the literature (specifically red hair and blue eyes, Valverde et al., 1995). 11 of the SNPs were selected from the NCBI dbSNP database (Column 7, Table 13).

TABLE 13

| Gene | Haploid Feature | Pos. | Marker | fCA(minor) | Type[1] | Source[2] | Pigment History |
|---|---|---|---|---|---|---|---|
| DCT | DCT-A | 2 | 702 | 0.15 | intron | dbsnp | none |
| DCT | DCT-A | 3 | 650 | 0.31 | intron | dbsnp | None |
| DCT | DCT-A | 4 | 675 | 0.21 | intron | dbsnp | None |
| MCIR | MC1R-A | 1 | 217438 | 0.07 | VAL__MET | reseqencing | None |
| MCIR | MC1R-A | 2 | 217439 | 0.07 | ARG__CYS | dbSNP, resequencing | Red hair[3] |
| MCIR | MC1R-A | 3 | 217441 | 0.07 | ARG__TRP | resequencing | Red hair[3] |
| OCA2 | OCA2-A | 1 | 217458 | 0.29 | Silent | dbSNP | None |
| OCA2 | OCA2-A | 2 | 886894 | 0.32 | Intron | resequencing | None |
| OCA2 | OCA2-A | 3 | 886895 | 0.13 | Intron | resequencing | None |
| OCA2 | OCA2-A | 1 | 888896 | 0.34 | Intron | resequencing | None |
| OCA2 | OCA2-B | 2 | 217452 | 0.04 | ARG__TRP | dbSNP | None |
| OCA2 | OCA2-B | 3 | 712052 | 0.23 | intron | dbSNP | None |
| OCA2 | OCA2-B | 4 | 886994 | 0.19 | intron | resequencing | none |
| OCA2 | OCA2C | 1 | 712057 | 0.18 | intron | dbSNP | None |
| OCA2 | OCA2C | 2 | 712058 | 0.11 | intron | dbSNP | None |
| OCA2 | OCA2C | 3 | 712060 | 0.06 | intron | dbSNP | None |
| OCA2 | OCA2C | 4 | 712064 | 0.01 | Silent | dbSNP | None |
| OCA2 | OCA2D | 1 | 712054 | 0.37 | intron | dbSNP | None |
| OCA2 | OCA2D | 2 | 712056 | 0.02 | intron | dbSNP | None |
| OCA2 | OCA2D | 3 | 886892 | 0.03 | intron | dbSNP | None |
| OCA2 | OCA2E | | 217455 | 0.42 | Silent | dbSNP | None |
| OCA2 | OCA2E | | 712061 | 0.02 | Silent | dbSNP | None |
| OCA2 | OCA2E | | 886892 | 0.19 | intron | resequencing | None |
| TYRP | TYRP-A | 1 | 886938 | 0.47 | intron | resequencing | None |
| TYRP | TYRP-A | 2 | 886943 | 0.47 | intron | resequencing | None |

Footnotes for Table 13:
[1]SILENT - no amino acid change, INTRON - SNP was found in non-coding sequence.
[2]DbSNP - candidate gene sequence is present in the NCBI:dbSNP as of Feb. 15, 2002. reseqeuncing - SNP sequence was discovered from the re-sequencing effort described in the text.
[3]Valverde et al., 1995; Frandberg et al., 1998 and Schioth et al., 1999.

Validation of the Penetrant Genetic Features. Having identified several penetrant feature SNP combinations of variable iris color shade, the analysis was extended to more completely investigate the associations of their penetrant genetic features with specific eye colors. From a contingency analysis of haplotypes and multilocus genotypes versus iris colors (blue, green, hazel, brown and black), numerous significantly associated alleles and allele combinations were identified (see Table 14 below). Chi-square adjusted residuals showed that many of the associations were quite strong at the haplotype level. For example, the OCA2-A TTAA was strongly associated with blue (p=0.0079, row 3, column 3, Table 14), but the OCA2-A CCAG and OCA2-B CGA alleles were strongly associated with brown (p=0.0008, row 4, column 3, Table 14; p=0.0024, row 11, column 3, Table 14, respectively).

TABLE 14

Effect Statistics for the Association of Genetic Feature Alleles with Iris Colors in the Caucasian Population.

| | Gene | Allele | p-value[1] | Association | Posterior Probability[2] | (N)[1] | Genotypes: | p-value[1] | Association | Posterior Probability[2] | (N)[1] |
|---|---|---|---|---|---|---|---|---|---|---|---|
| 1 | MC1R-B | CCC | 0.0458 | Hazel | 0.369 | 499 | CCC/CCC | 0.0327 | Hazel | 0.344 | 186 |
| 2 | | Total | Insig. | | | 648 | Total | Insig. | | | 324 |

TABLE 14-continued

Effect Statistics for the Association of Genetic Feature Alleles with Iris Colors in the Caucasian Population.

| | Gene | Allele | p-value[1] | Association | Posterior Probability[2] | (N)[1] | Genotypes: | p-value[1] | Association | Posterior Probability[2] | (N)[1] |
|---|---|---|---|---|---|---|---|---|---|---|---|
| 3 | OCA2-A | TTAA | 0.0079 | Blue | 0.382 | 423 | TTAA/TTAA | 0.0194 | Blue | 0.415 | 147 |
| 4 | | CCAG | 0.0008 | Brown | 0.447 | 85 | TTAA/CCAG | 0.0613 | Brown | 0.386 | 56 |
| 5 | | TTAG | 0.0045 | Brown | 0.627 | 13 | TTAA/TTAG | 0.0006 | Brown | 0.735 | 11 |
| 6 | | | | | | | TTAA/CTAG | 0.0167 | Blue | 0.795 | 5 |
| 7 | | | | | | | CCAG/CCAG | 0.0488 | Brown | 0.584 | 7 |
| 8 | | | | | | | CCAG/CCGG | 0.0050 | Brown | 0.649 | 11 |
| 9 | | Total | 0.0453 | | | 606 | Total | 0.0053 | | | 303 |
| 10 | OCA2-B | CAA | 0.0269 | Blue | 0.381 | 354 | CAA/CAA | 0.0255 | Hazel | 0.375 | 112 |
| 11 | | CGA | 0.0024 | Brown | 0.389 | 131 | CAA/CGA | 0.0314 | Blue | 0.443 | 70 |
| 12 | | CAC | 0.0200 | Brown | 0.386 | 83 | CGA/CAC | 0.0024 | Brown | 0.542 | 24 |
| 13 | | CGC | 0.0441 | Green | 0.417 | 12 | CGA/CGC | 0.0006 | Green | 0.500 | 6 |
| 14 | | Total | 0.0058 | | | 606 | Total | 0.02148 | | | 303 |
| 15 | TYRP-B | TC | 0.001 | Blue | 0.403 | 234 | none | — | — | — | — |
| 16 | | Total | 0.0451 | | | 660 | Total | Insig. | | | 330 |
| 17 | DCT-B | CTG | 0.0133 | Brown | 0.362 | 94 | GCA/CTG | 0.006 | Hazel | 0.100 | 53 |
| 18 | | GTG | 0.0249 | Hazel | 0.571 | 7 | GCA/GTA | 0.0527 | Blue | 0.625 | 8 |
| 19 | | | | | | | GCA/GTG | 0.0090 | Hazel | 0.667 | 6 |
| 20 | | | | | | | CCA/CTG | 0.0044 | Blue | 0.412 | 17 |
| 21 | | Total | Insig. | | | 660 | Total | Insig. | | | 330 |
| 22 | OCA2-C | GGAA | 0.0013 | Blue | 0.382 | 463 | GGAA/GGAA | 0.0086 | Blue | 0.4045 | 178 |
| 23 | | TGAA | 0.0125 | Brown | 0.4058 | 69 | GGAA/TAAA | 0.0089 | Hazel | 0.5385 | 13 |
| 24 | | TAAA | 0.0475 | Hazel | 0.4375 | 16 | TGAA/TAAA | 0.0033 | Brown | 1.0000 | 3 |
| 25 | | | | | | | GGGA/GGGA | 0.0500 | Brown | 0.3333 | 3 |
| 26 | | Total | 0.0189 | | | 606 | Total | 0.0547 | | | 303 |
| 27 | OCA2-D | AGG | 0.0468 | Hazel | 0.2832 | 346 | AGG/AGG | 0.0445 | Hazel | 0.3148 | 108 |
| 28 | | GGG | 0.0222 | Brown | 0.3377 | 231 | AGG/AGC | 0.0202 | Brown | 0.6667 | 6 |
| 29 | | | | | | | GGG/GGG | 0.0509 | Brown | 0.3913 | 46 |
| 30 | | Total | Insig. | | | 606 | Total | Insig. | | | 303 |
| 31 | OCA2-E | GCA | 0.0004 | Brown | 0.4828 | 58 | ACG/GCA | 0.0436 | Brown | 0.4048 | 42 |
| | | | | | | | GCA/GCA | 0.0034 | Brown | 1.0000 | 3 |
| 32 | | | | | | | GCA/GCG | 0.0060 | Brown | 0.8000 | 5 |
| 33 | | Total | Insig. | | | 614 | Total | Insig. | | | 307 |

Footnotes for Table 14:
[1] Pearsons Chi-square statistic p-value. Only alleles and allele combinations that were significantly associated with an iris color are shown (n > 2).
[2] Bayesian posterior probability of correct eye color classification using allele frequency in the eye color group as the class conditional probability.

Analysis at the level of the multilocus genotypes showed that each of the penetrant genetic feature SNP combinations were also statistically associated with eye colors (i.e. none of the 8 SNP combination is missing an entry in column 8, Table 14). Though their alleles were associated with iris color shades, the chi-square statistic of contingency analysis for haplotype or multilocus alleles of the DCT-B, TYR-A, OCA2-D and OCA2-E features were not significant. For example, the DCT-B total p-value was insignificant at the haplotype (row 21, column 3, 8 Table 14) and multilocus genotype levels (row 21, column 8, Table 14). Nonetheless, adjusted residuals for two (2) of the DCT-B haplotypes show that these particular alleles were strongly associated with eye colors even though the total chi-square statistic was not significant (CTG with brown, p=0.0133, row 17, column 3, Table 14 and GTG with hazel, p=0.0249, row 18, column 3, Table 14). The same was observed for other feature SNP combinations that were not associated with specific iris colors but were associated with iris color shade; the OCA2-D AGG genetic feature with Hazel irises (p=0.0468, row 27, column 3, Table 14), the OCA2-D GGG genetic feature with brown irises (p=0.0222, row 28, column 3, Table 14) and the OCA2-E GCA genetic feature with brown irises (p=0.0004, row 31, column 3, Table 14).

Given the sample size and the association strength, the most important genetic features for predicting brown irises were found in the OCA2-D, OCA2-E and DCT-B feature SNP combinations, and the most important for blue or green iris colors were found in the MC1R-B and TYRP-B feature SNP combinations (columns 5 and 6, Table 14). Even though there were twice as many genetic features of blue irises counted as for brown (1474 vs. 664, counting down columns 6 and 11 for each color, Table 14), there were half as many types of genetic features of brown as for blue irises (4 versus 8, counting down column 4 for each color, Table 14). This suggests that the diversity of haplotypes associated with brown irises was significantly greater than that of the haplotypes associated with blue irises. Most of the haplotypes and multilocus genotypes for the feature combinations were even more dramatically associated with eye colors in a multi-racial sample (data not shown), presumably because the variants associated with darker irises were enriched in those racial groups of the world that are of darker average iris color than Caucasians.

The associations at the level of the multilocus genotypes for these penetrant genetic features suggest that some of the haplotype alleles contribute towards the dominance component of iris color variance. For example, though the OCA2-A TTAA haplotype is strongly associated with blue irises (p=0.0079, row 3, column 3, Table 14) and the OCA2-A TTAG haplotype is strongly associated with brown irises (p=0.0045, row 5, column 3, Table 14), the OCA2-A TTAA/TTAG multilocus genotype was strongly associated with brown irises, not blue (p=0.0006, row 5, column 8, Table 14). Not all of the dominance component contributions were towards darker eye colors. For example, OCA2-B CAA was strongly associated with blue irises (p=0.0269, row 10, column 3, Table 14) and OCA2-B CGA with brown irises (p=0.0024, row 11, column 3, Table 14) but the OCA2-B CAA/CGA multilocus genotype was associated with blue, not brown irises (p=0.0.0314, row 11, column 8, Table 14).

A contingency table was constructed and the multilocus genotypes were plotted to visualize the lower-dimensional inter-relationships between multilocus genotypes of the penetrant genetic features and iris colors, as well as to encode individuals. From this analysis, it was clear that genotypes of penetrant genetic features of Blue, Green, and Hazel irises share more profile similarity to one another than to those of brown irises. A plot of genotypes and trait values that are truly related to one another would produce a plot pattern that makes intuitive biological sense. In the COA plot, blue, green, hazel, and brown irises plotted as profile functions of genetic feature genotypes are found along a clockwise progression around the centroid. This is the order in which the concentrations of brown pigment (eumelanin) increases. Because the genes measured in this analysis are involved in the production of this pigment, this pattern makes intuitive sense since. Further, the multilocus genotypes of the penetrant feature SNP combinations were more distantly removed from the centroid than genotypes of combinations that were not as significantly associated (Table 14). This was as expected since the distance from the centroid is proportional to the contribution of a genotype towards the overall chi-square statistic in the original contingency table.

To confirm the results and determine the role of specific mutations in the determination of eye color variation, a nested contingency analysis was performed on haplotype cladograms of the penetrant feature SNP combinations (Templeton et al., 1987). Haplotype cladograms of all genetic features are inlaid with variants that are functionally interconnected through evolutionary time. The evolutionary framework will often ascribe patterns to present day trait associations that are derived from the evolutionary history of the alleles and in so doing, may suggest a biological, not merely statistical relevance for a genetic association. Significant cladogram based pattern was identified for the associations of OCA2-A, OCA2-B, OCA2-C, OCA2-D, and TYRP-A alleles (see Table 15 below), suggesting that mutations relevant for iris color occurred relatively early in the evolution of these gene sequences. Two of the feature SNP combinations (OCA2-B and OCA2-C) had more than one functionally relevant mutation with a discernable evolutionary history, but for most of the others, the largest amount (though not all) of the variability in iris colors could be traced back to branchings created by change at a single locus of the feature combination. No significant cladogram based pattern was detected for the MC1R-A, OCA2-E or DCT-B feature SNP combinations. For these, it appears that the alleles associated with iris color have independently evolved at a time later in the evolutionary history of their gene sequences than for the OCA2-A, OCA2-B, OCA2-C OCA2-D and TYRP-A alleles.

TABLE 15

Nested Contingency Analysis of Haplotype Cladograms for the Identified Genetic Features of Variable Eye Color.

| Feature | Contingency Significance | Allele partition | p-value[1] | Site(s).[2] |
|---|---|---|---|---|
| MC1R-A | none found | — | — | — |
| OCA2-A | Between 3-Step Clades | (CCAG + CCGG + TCAG + TCGG + TCAA) vs. (TTGG + TTAG + CTAG + CTAA + TTAA) | 0.0011 | 2 |
| OCA2-B | Within 1-Step Clades | CGA vs. CAA | 0.0012 | 2 |
| | Between 2-Step clades | (TAC + CAC + CGC) vs. (CGA + CAA + TAA + TGA) | 0.0246 | 3 |
| OCA2-C | Between 3-Step Clades | (TGAA + TAAA + TAAG) vs. (GGAA + GAAA + GGGA + GAGA + GGAG) | 0.0014 | 1 |
| | Within 1-Step Clades | TGAA vs. TAAA | 0.0263 | 2 |
| OCA2-D | Between 3-Step Clades[3] | (AGC + GGC) vs. (AGG + GGG + AAG + GAG) | 0.0052 | 3 |
| OCA2-E | none found | — | — | — |
| TYRP-A | Between 2-step Clades | (CC + CT + TT) vs. TC | 0.0136 | 1 |
| DCT-B | none found | — | — | — |

Footnotes for Table 15:
[1]Chi-square statistic p-value, degrees of freedom were 3 for each analysis.
[2]Locus within the SNP combination that the nested contingency analysis shows significant variations in eye colors can be traced back to. This information is also present in the Allele partition column.
[3]This is a good example of the value this nested cladogram analysis afforded. Though two alleles of the OCA2-D SNP combination (AGG and GGG, rows 27 and 28, column 3, Table 14) were associated with iris colors from Chi-square adjusted residual analysis, the Chi-square statistic for contingency analysis of all of the alleles together was not significant (row 30, column 3, Table 14). The nested cladogram analysis showed that these two sequences are evolutionary neighbors and suggested that the GG 3' end of the OCA2-D combination is strongly associated with darker iris colors (p = 0.0014, Table 15). Evidently, this significance was lost in the noise produced at the pan-allele level by the lack of association between the other four haplotype alleles and iris colors.

Latent genetic features. Because the prevalence of each iris color trait was relatively high in the sample group as well as in the general population, and because the allele frequencies of most of the SNPs we studied were also relatively high, the heritibility of iris colors would be expected to be reasonable for the detection of SNP associations within the context of a case-control study design (Culverhouse et al., 2002). Nonetheless, a major drawback of the genome-based case control study design (given the analytical methods that have been employed so far) is the lack of power to detect alleles that exclusively or substantially contribute towards genetic variance through the epistatic component (Culverhouse et al., 2002). SNPs that were not part of the penetrant feature SNP combinations described in Table 12 may either not contribute towards iris color variance, or may contribute through epistatic means. Though undetectable with the case-control design, epistatic components can more easily be detected in linkage studies than in case control studies because purely (or largely) epistatic models give rise to excess allele sharing among affected sibs in linkage analysis. It was reasoned that a racial comparison of pigmentation allele frequencies between Caucasians and Africans/Asians represent an extreme case of a very simple linkage study, where the racial groups are equivalent to sibs of a family pedigree. In this case, the linkage is considered within the context of an evolutionary, rather than familial scale, because individuals of the latter two races exhibit darker average iris color than Caucasians. Thus, to identify those SNPs that may contribute towards the epistatic component of iris color variance, what were screened were the SNPs that were not part of the penetrant feature SNP combinations described in Table 12 for alleles that were enriched in either Caucasians (n=100 new individuals, not yet analyzed) or the African/Asian combined (n=130 new individuals, not yet analyzed) groups. Though most alleles in non-pigmentation genes do not show dramatic minor allele frequency differences between the two racial groups (Frudakis et al., 2002; for example, Table 16B below), alleles of many of the SNPs not part of the penetrant feature SNP combinations of Table 12 show unusual minor allele frequency differences between the two racial groups (Table 16A below). It was inferred that these differently shared SNP alleles may contribute towards the epistatic component of iris color variance. Though haplotype alleles are generally more predictive for trait value than individual SNP alleles, it is not possible to determine which alleles of these SNP combinations contribute most towards this variance. Thus, they were combined into arbitrary SNP combinations, the components of which were in linkage disequilibrium, and were termed "latent feature SNP combinations" of variable iris colors and their haplotype (and multilocus genotype) alleles "latent genetic features" of variable iris color.

TABLE 16A

Allele Frequency Difference for Alleles of Latent Haploid Genetic Features among Racial Groups.

| Gene | Marker | $F_{ca}^1$ | $F_{aa}^2$ | $F_{as}^3$ | $F_{light}^4$ | $F_{dark}^5$ |
|---|---|---|---|---|---|---|
| ASIP | 560 | 0.01 | 0 | 0.10 | 0.01 | 0.03 |
| ASIP | 552 | 0.19 | 0.58 | 0.23 | 0.19 | 0.49 |
| ASIP | 559 | 0.07 | 0.28 | 0 | 0.07 | 0.21 |
| ASIP | 468 | 0.20 | 0.80 | 0.40 | 0.20 | 0.70 |
| DCT | 657 | 0.28 | 0.29 | 0.90 | 0.28 | 0.44 |
| DCT | 674 | 0.36 | 0.56 | 0.63 | 0.36 | 0.58 |
| DCT | 632 | 0.01 | 0 | 0 | 0.01 | 0 |
| DCT | 701 | 0.21 | 0.32 | 0.10 | 0.21 | 0.27 |
| DCT | 710 | 0.53 | 0.37 | 0.57 | 0.53 | 0.42 |
| OCA2 | 217456 | 0.17 | 0.03 | 0.03 | 0.17 | 0.03 |

TABLE 16A-continued

Allele Frequency Difference for Alleles of Latent Haploid Genetic Features among Racial Groups.

| Gene | Marker | $F_{ca}^1$ | $F_{aa}^2$ | $F_{as}^3$ | $F_{light}^4$ | $F_{dark}^5$ |
|---|---|---|---|---|---|---|
| SILV | 656 | 0.17 | 0.49 | 0.20 | 0.17 | 0.42 |
| SILV | 662 | 0.46 | 0.22 | 0.60 | 0.46 | 0.32 |
| SILV | 637 | 0.03 | 0 | 0.03 | 0.03 | 0.01 |
| TYR | 278 | 0.73 | 0.42 | 0.53 | 0.73 | 0.45 |
| TYR | 386 | 0.72 | 0.46 | 0.50 | 0.72 | 0.46 |
| TYR | 217480 | 0.17 | 0.03 | 0.03 | 0.17 | 0.03 |
| TYR | 951497 | 0.24 | 0.48 | 0.37 | 0.24 | 0.45 |
| TYR | 217468 | 0.64 | 0.10 | 0 | 0.64 | 0.08 |
| TYR | 217473 | 0.29 | 0.09 | 0.02 | 0.29 | 0.07 |
| TYRP1 | 217485 | 0.40 | 0.10 | 0.07 | 0.40 | 0.10 |
| TYRP1 | 217486 | 0.86 | 0.27 | 0.03 | 0.86 | 0.22 |
| TYRP1 | 869787 | 0 | 0.07 | 0 | 0 | 0.05 |
| TYRP1 | 869745 | 0 | 0.07 | 0 | 0 | 0.05 |
| TYRP1 | 886933 | 0.15 | 0.41 | 0.23 | 0.15 | 0.37 |
| TYRP1 | 886937 | 0.16 | 0.10 | 0 | 0.16 | 0.08 |
| TYRP1 | 886942 | 0 | 0.06 | 0 | 0 | 0.04 |
| TYRP1 | 869787 | 0 | 0.07 | 0 | 0 | 0.05 |

TABLE 16B

| GENE | MARKER | $F_{ca}$ | $F_{aa}$ | $F_{as}$ | $F_{light}$ | $F_{dark}$ |
|---|---|---|---|---|---|---|
| SILV | 704 | 0.66 | 0.59 | 0.77 | 0.66 | 0.63 |
|  | 699 | 0.30 | 0.11 | 0.87 | 0.30 | 0.30 |

Footnotes for Table 16B:
[1] Frequency in the Caucasian racial group (N = 100).
[2] Frequency in the African racial group (N = 100).
[3] Frequency in the Asian racial group (N = 30).
[4] The Caucasian group (N = 100) is designated the light (blue, green or hazel) iris colored race since the frequency of these iris colors is greatest in this group.
[5] The African and Asian groups (N = 130) is designated the dark (black and brown) iris colored race since the frequency of blue, green and hazel irises are lowest in this group.

Feature Modeling and Classifier Construction. Using the penetrant genetic features as independent classifiers, Bayesian posterior probabilities of correct classification approached 50% for some, but fell within the 30%-40% range for most (columns 5 and 10, Table 14). These results imply that the determination of variable iris colors is complex and suggest that though the alleles of the penetrant feature SNP combinations are associated with iris color variance, any one component on its own explains but a minor fraction of this variance and its predictive power as an independent classifier is too low for field use.

Weighted quadratic classification using only the penetrant genetic features. To generate a complex model by which to explain more iris color variance, to an extent that accurate inferences could be made, a weighted quadratic classification algorithm was developed based on standard coordinates from a correspondence analysis. The penetrant genetic features were first used to compute and weight a variance-covariance matrix from 330 Caucasian individuals. This matrix was applied for a blind, quadratic discriminate classification of iris colors in 286 other Caucasians of known but concealed iris color. For the first analysis two groups were defined; a light iris shade group defined as individuals of blue, green or hazel irises, and the dark iris shade group defined as individuals of brown or black irises. At the level of the multilocus genotypes (gene-wise genotypes), an overall accuracy of 98% for this discrimination was obtained. The sensitivity for dark iris color shades was 100% and the sensitivity for light eye color shades was 97% (reading along the rows, Table 17A below). The light iris classification was 100% accurate and the dark iris classification was 94% accurate (reading down the columns, Table 17B below). Using this method at the level of individual SNP alleles, SNP genotypes or individual haplotype alleles produced lower accuracies (with accuracies in increasing order), suggesting that the highest level of intragenic allele complexity is required for accurate inference of eye color shade and that increasing levels of complexity offer successively greater predictive power. Using the method with multilocus genotypes to infer actual eye colors, rather than just eye color shade, what was obtained was 100% sensitivity for blue iris classification, 69% sensitivity of brown iris classification, 100% sensitivity of green iris classification and 84% sensitivity of hazel iris classification (reading along rows, Table 17B). The accuracy of blue iris classification was 67%, of brown iris classification 100%, of green iris classification 100% and of hazel iris classification 74% (reading down the columns, Table 17B). Using simulation to estimate the inference power of the quadratic classifier we obtained a log likelihood of r=1.96. In effect, the classifier was remarkably accurate and sensitive, with good inference power, but its deficiency was apparent in the misclassification of brown and hazel iris individuals into the blue iris group.

TABLES 17A and 17B

Correspondence Analysis Assisted Quadratic Discriminate-Based Classification of Iris Colors using the Penetrant Genetic Features of Variable Iris Color. (A) Probability table for classification between dark (black and brown) versus light (blue, green and hazel) iris colors; and (B) Probability table for classification among the various iris colors.

TABLE 17A

|  | Light Iris Classification[1] | Dark Iris Classifications[1] |
|---|---|---|
| Individuals of Light Irises | 97.5% (197) | 2.5% (5) |
| Individuals of Dark Irises | 0 | 100 (84) |

TABLE 17B

|  | Blue Iris Classification[1] | Brown Iris Classification[1] | Green Iris Classification[1] | Hazel Iris Classification[1] |
|---|---|---|---|---|
| Individuals of Blue Irises | 100% (97) | 0 | 0 | 0 |
| Individuals of Brown Irises | 19% (40) | 69% (141) | 0 | 12% (24) |
| Individuals of Green Irises | 0 | 0 | 100% (32) | 0 |
| Individuals of Hazel Irises | 14% (12) | 0 | 1% (1) | 84% (69) |

Footnotes for Tables 17A & 17B:
[1]Percent classified is shown, with the number of individuals classified shown in parentheses.

By adding the latent genetic features to this analysis (latent+penetrant genetic features), the optimal weighting strategy produced a covariance matrix that blindly generalized to the same 286 Caucasians with 100% accuracy and sensitivity for discrimination of light versus dark iris color shades. The optimal model also generalized to this sample with 91.3% accuracy for the inference of actual iris colors (261/286 correctly classified; along diagonal of Table 18A below). The Specificities were: blue irises 81% (96/118), brown irises 97.4% (76/78), green irises 96.8% (30/31) and hazel irises 100% (59/59) (reading down columns of Table 18A). The sensitivities were: individuals of blue irises 99% (96/97), brown irises 90.5% (76/84), green irises 100% (30/30) and hazel irises 78.7% (59/75). Using simulation to estimate inference power of the quadratic classifier, we obtained a log likelihood of r=2.22 for classification into the proper iris color group. Though it is true that markers over-represented in racial groups of average darker iris colors would help the classifier artificially infer eye color in a multi racial sample, it is not true that any such markers would help with the inference of iris colors in Caucasians unless they were functionally relevant for human iris coloration. That these markers contributed towards the classifications within Caucasians suggests that they are functionally related to, or linked to markers functionally related to iris color determination.

TABLES 18A and 18B

Correspondence Analysis Assisted Quadratic Discriminate-Based Classification of Iris Colors using Both Penetrant and Latent Genetic Features of Variable Iris Color. (A) Probability table for classification between dark (black and brown) versus light (blue, green and hazel) iris colors. (B) Probability table for classification among the various iris colors.

TABLE 18A

|  | Blue Iris Classification[1] | Brown Iris Classification[1] | Green Iris Classification[1] | Hazel Iris Classification[1] | Total |
|---|---|---|---|---|---|
| Individuals of Blue Irises | 99.0% (96) | 0 | 1.0% (1) | 0 | 97 |
| Individuals of Brown Irises | 9.5% (8) | 90.5% (76) | 0 | 0 | 84 |
| Individuals of Green Irises | 0 | 0 | 100% (30) | 0 | 30 |
| Individuals of Hazel Irises | 18.7% (14) | 2.7% (2) | 0 | 78.7% (59) | 75 |
| Total | 118 | 78 | 31 | 59 | 286 |

TABLE 18B

|  | Light Iris Classification[1] | Dark Iris Classifications[1] |
|---|---|---|
| Individuals of Light Irises | 100% (197) | 0 |
| Individuals of Dark Irises | 0 | 100% (84) |

Footnotes for Tables 18A and 18B:
[1]Percent classified is shown, with the number of individuals classified shown in parentheses.

One important advance made here is algorithmically capturing the epistatic component. The present work showed that there is a minimal set of 25 penetrant SNPs, of 8 multilocus contexts in 4 genes that are required for minimal inference accuracy. However, a complete set of 57 SNPs, of 19 multilocus contexts (both penetrant and latent), in all 8 of the genes is needed for accurate inference. That latent genetic features are needed for accurate inference suggests that there is a significant epistatic component to iris color variance in the Caucasian population. The agouti signaling protein (ASIP) harbored four and the silver locus (SILV) harbored three such polymorphisms, each of which was arbitrarily combined into a single latent feature SNP combination. DCT and TYR harbored five and six such polymorphisms, respectively. That no penetrant genetic features were identified in ASIP, SILV or TYR suggests that these genes contribute towards iris color variance largely through epistatic means. The latent features are not equivalently predictive, and to capture the epistatic component during classification, weights were randomly ascribed to different alleles in different contexts and selected the combination that allowed for the most optimal quadratic discrimination.

The results suggest that there is much to be learned about the genetics of iris color from a detailed inspection of this optimal weighting scheme. At present, it is difficult to fully understand the mechanism by which the features fit together the way they do in the optimal COA-derived quadratic classifier model. However, it is known that they do fit together and that the fit is of maximal practical utility for the inference of iris colors. The results suggest that iris color is indeed a complex genetic trait, the "whole" of which was empirically determined to be greater than the sum of its "parts".

On a more general level, the results illustrate a seemingly obvious but interesting concept: simple genetics approaches are useful for ascribing trait associations for individual genes and haplotypes within them, but because most human traits are complex, complex genetics tools are required for their use in the development of accurate classification tests. Given the sources of error for this work, including genotyping errors, errors in self-reported iris color and statistical haplotype inference, it is quite remarkable that we could achieve 97% classification accuracy with a combined sample size of 550 for such a complex trait. In terms of feature modeling, almost identical results were obtained using a classification tree (CART-based) method, even though the cost function of the method used herein relates genotypes (haplotype pairs) to trait values in a more direct way than CART. Thus, it appears that the methods employed herein are substantiated by other analytical methodologies and may be promising for the generation of other complex genetics classifiers, for example pharmacogenomics or complex disease genetics classifiers.

Though 97% accurate, the present classifier was not perfect and there are genes part of other processes, developmental and cellular, that could explain the remaining 3% of iris color variance. The genes part of these processes have not yet been tested. Studies in *Drosophila* have implicated over 85 genes in iris pigmentation (Ooi et al., 1997; Lloyd et al., 1998) and far more than 8 genes have been implicated in oculocutaneous albinism in model vertebrates. That almost all of iris color variance in human beings can be explained by polymorphisms in eight (8) carefully selected genes, given the biological complexity of pigmentation, illustrates that just because a gene is crucial for a process (i.e. its mutation causes loss of function) does not necessarily mean that natural distributions of this process among individuals is related to natural polymorphisms in this gene. By way of analogy, there are many ways to break an automobile engine—removing a water hose for example—but virtually none of the variability in engine performance is caused by variability in hose characteristics. Certain parts of the complex genetics "engine" seem to have become sinks for accumulating functionally relevant polymorphisms during the evolutionary branching of our ancestors.

In fact, one of the surprising findings of this work was that of all of the genes tested, the OCA2 gene explained by far the most iris color variance. Five (5) of the eight (8) feature SNP combinations were from the OCA2 gene and seventeen (17) of the twenty-five (25) SNPs part of these penetrant feature SNP combinations were OCA2 SNPs. To date, no polymorphism screens within OCA2 have yet been described (though they had been called for—see Sturm et al., 2001) and this work is the first indication of the importance this gene has for natural iris color pigmentation. The OCA2 gene product localizes to the melanosomal membrane and resembles an *E. coli* Na+/H+ anti-porter. Though TYR activity correlates perfectly with eumelanin content in melanosomes (Iozumi et al., 1993), its activity is thought to be manipulated by the OCA2 gene product through the control of intramelanosomal pH (Ancans 2001b). Tyrosinase taken from dark and light skin functions identically in-vitro, but is highly pH dependent and melanocytes from white skin are more acidic than those from black (Fuller et al., 2001, Ancans et al., 2001a). Given these observations, it seems that OCA2 is the primary modifier of TYR activity, which is consistent with our statistical results. It is interesting to note that at the level of the cladogram analysis, four of the five allele associations were obtained for OCA2 feature SNP combinations. It is also interesting to note that the diversity of alleles associated with darker iris colors is significantly greater than that of alleles associated with lighter iris colors. These observations combined suggest that lighter colored irises branched from darker colored irises relatively long ago in human evolutionary time, and that modifications to the OCA2 gene may have been instrumental in this branching. The generally accepted anthropological and molecular view of the origin of modern humans from Africa states that Northern Europeans branched from African founders. Our results suggest that the reason lighter colored irises are almost exclusive to individuals of Northern European ancestry is in large part due to relatively ancient (and numerous) modifications of the OCA2 expression product. The fact that brown classifications were far more accurate relative to blue before, but not after, the addition of the latent genetic features to the classifier model may indicate that blue irises are subject to more epistasis than dark, and that dark eyes tend to be relatively (though not strictly speaking) dominant.

When applied to a multi-racial sample, the penetrant feature (as well as the combined penetrant+latent feature) classifier performed with substantially better accuracy than when applied only to Caucasians. Since most non-Caucasian ethnic groups exhibit low variability in iris colors (on average of darker shade than Caucasians) this improvement may not seem surprising. However, though an incorrect solution would not necessarily be more accurate when applied to individuals of the world's various populations, notwithstanding genetic heterogeneity, a correct solution would be. The reason for this is that if alleles associated with darker iris color in Caucasians are deterministic, or linked to deterministic alleles for melanin production and iris color, and if it is assumed that the between race component of iris color variance is low, the frequencies of these alleles should be greater in populations of average darker iris color. Because the accuracy of our solution increases when applied pan-ethnically, the results suggest that the associations described are functionally relevant. Since most of the SNPs are intron or silent changes, it is inferred that the alleles we have described are statistically linked with other unidentified alleles, or are functional in ways other than through amino acid changes (such as RNA transcription, degradation, localization etc.).

Interestingly, the classifier generated for iris color does not accurately extend for classification of hair color or skin shade within Caucasians. In fact, this is what one would expect from a good complex genetic model for variable Caucasian iris color, since iris, skin and hair color are known to be independently inherited (and distributed) within this racial group. A study similar to the one described herein for hair color was conducted and though there is about 33% overlap between the SNP marker sets, the sets are distinct (data be presented elsewhere). It is assumed that the classifier generated here would be, at least in part, extendable to other racial groups, such as for the discrimination between green, hazel and brown irises in individuals of African descent. Whether or not this is true is a subject for further study.

As the first genetic solution capable of ascribing qualitative characteristics from anonymously donated DNA, the results represent an important achievement. First, they illustrate one method for modeling complex human traits from high-density genomics data sets. Second, as a forensics tool, the solution could be used to guide criminal or other forensics investigations (in this case, multilocus genotype combinations that are relatively ambiguous could be classified with regard to iris color shade and conditional probability statements offered for specific iris color classifications). Third, as a research tool, the common haplotypes identified may help researchers more accurately define the complex genetics risks for pigmentation related diseases such as cataracts and melanoma.

Figure 12:
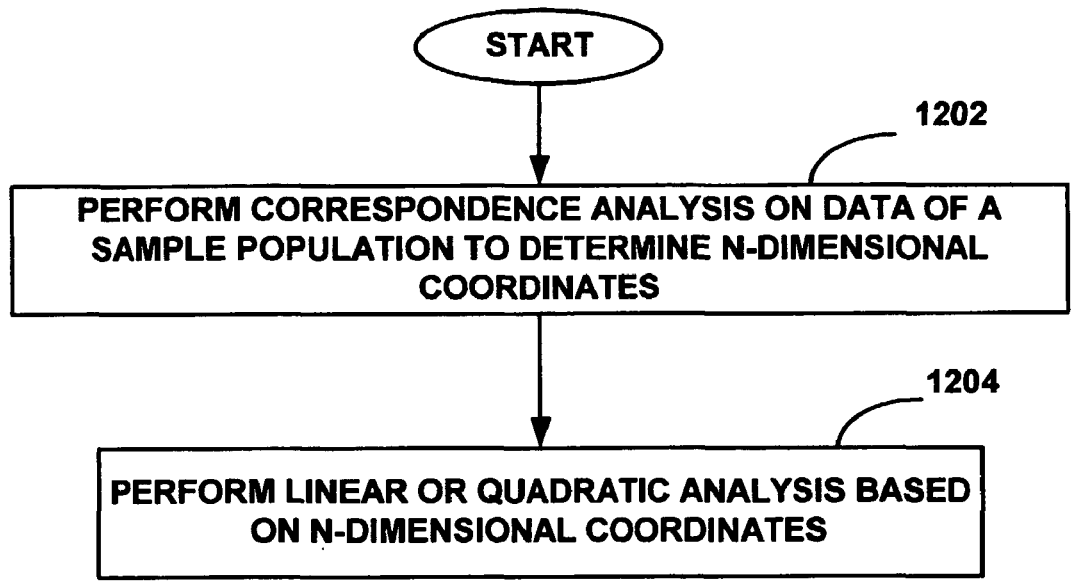
FIG. 12 is a flowchart for describing a method for use in genetics classification based on both COA and linear or quadratic analysis.

FIG. 12 is a flowchart which more generally describes the above-detailed method for use in genetics classification which is based on both correspondence analysis (COA) and linear or quadratic analysis. The method is employed in connection with data from a sample population which includes counts of individuals in the sample population associated with both a particular diploid haplotype pair and a particular genetic trait class (i.e. for each combination of each diploid haplotype pair of at least two genes and each genetic trait class of a genetic trait). Beginning at a start block 1200 of FIG. 12, at least part of a correspondence analysis (COA) is performed on the data from the sample population, so as to determine a first plurality of n-dimensional coordinates for each of diploid haplotype pair and a second plurality of n-dimensional coordinates for each genetic trait class (step 1202). Next, a linear or quadratic analysis is performed using the first and the second pluralities of n-dimensional coordinates determined from the COA and diploid haplotype pairs of the at least two genes from an individual sample taken from outside of the sample population (step 1204). Advantageously, the individual sample may be accurately classified into one of the genetic trait classes based on the analyses.

It is to be understood that the above is merely a description of preferred embodiments of the invention and that various changes, alterations, and variations may be made without departing from the true spirit and scope of the invention as set for in the appended claims. Few (if any) terms or phrases in the specification and claims have been given any special particular meaning different from the plain language meaning to those skilled in the art, and therefore the specification is not to be used to define such "plain language" terms in an unduly narrow sense.

What is claimed is:

1. A method performed on a computer device for genetically classifying an individual outside of a sample population based on data from the sample population, the data from the sample population including, for each combination of each diploid haplotype pair of at least two genes and each genetic trait class of a genetic trait, a count of individuals in the sample population associated with both a diploid haplotype pair and a genetic trait class, the method being based on a correspondence analysis on the data from the sample population which provides a first plurality of n-dimensional coordinates for each diploid haplotype pair and a second plurality of n-dimensional coordinates for each genetic trait class, the method comprising the acts of:
performing, by the computer device, a linear or quadratic analysis on the data by:
producing, by the computer device, a variance-covariance matrix based on the first and the second pluralities of n-dimensional coordinates provided from the correspondence analysis;
producing, by the computer device, a classification decision for an individual sample of the individual based on diploid haplotype pairs of the at least two genes of the individual sample and the variance-covariance matrix, for classifying the individual sample into the one of the genetic trait classes; and
outputting, from the computer device, the classification decision for display to a user.

2. The method of claim 1, wherein the act of performing the correspondence analysis comprises the further act of:
calculating, by the computer device, a mass and an inertia for each diploid haplotype pair and for each genetic trait class.

3. The method of claim 1, wherein each diploid haplotype pair comprises a statistically significant diploid haplotype pair.

4. The method of claim 1, wherein the act of performing the correspondence analysis comprises the further acts of:
for each gene of a plurality of genes:
generating a data table having rows corresponding to the diploid haplotype pairs in the gene and columns corresponding to the genetic trait classes, such that each data cell of the data table contains the count of individuals in the sample population that associate with both the diploid haplotype pair and the genetic trait class.

5. The method of claim 1, wherein the genetic trait comprises eye color.

6. The method of claim 1, which is Performed by the computer device in accordance with computer instructions stored in a computer readable medium.

7. The method of claim 1, wherein the genetic trait comprises eye color.

8. A method performed on a computer device for use in genetics classification comprising the acts of:
performing, by the computer device, at least part of a correspondence analysis which includes, for each gene of a plurality of genes, the further acts of:
producing a data table having rows corresponding to a plurality of diploid haplotype pairs in the gene and columns corresponding to a plurality of genetic trait classes of a genetic trait, such that each data cell of the data table contains a count of individuals of a sample population that associate with both the corresponding diploid haplotype pair and the corresponding genetic trait class; for each table created for each gene:
calculating, by the computer device, a first plurality of n-dimensional coordinates for each diploid haplotype pair based on data in the data table;
calculating, by the computer device, a second plurality of n-dimensional coordinates for each genetic trait class based on data in the data table;
calculating, by the computer device, for an individual sample outside of the sample population, n-dimensional coordinates for diploid haplotype pairs of the plurality of genes of the individual sample;
determining, by the computer device, that coordinates associated with the individual sample are closest to coordinates associated with a specific one of the genetic trait classes;
producing, by the computer device based on the determining step, a classification decision for the individual sample for classification of the individual sample into the specific genetic trait class; and
outputting, from the computer device, the classification decision for display to a user.

9. The method of claim 8, comprising the further act of:
performing a linear or quadratic classification analysis based on the first and the second pluralities of the n-dimensional coordinates.

10. The method of claim 8, comprising the further acts of:
performing a linear or quadratic classification analysis based on the first and the second pluralities of the n-dimensional coordinates by creating a variance-covariance matrix based on the first and the second pluralities of n-dimensional coordinates determined from the correspondence analysis.

11. The method of claim 8, comprising the further acts of:
calculating, by the computer device, a mass and an inertia for each diploid haplotype pair and for each genetic trait class.

12. The method of claim 8, comprising the further act of:
causing, by the computer device, one or more plots to be produced for display based on the first and the second pluralities of n-dimensional coordinates, the one or more plots identifying the diploid haplotype pairs and the genetic trait classes.

13. The method of claim 8, wherein the act of determining that coordinates associated with the individual sample are closest to coordinates associated with a specific one of the genetic trait classes comprises the further acts of:
calculating, by the computer device, an average distance between coordinates; and
identifying that the calculated average distance for the specific genetic trait class is a minimum relative to calculated average distances associated with each one of the other genetic trait classes.

14. The method of claim 8, wherein the act of determining that coordinates associated with the individual sample are closest to coordinates associated with a specific one of the genetic trait classes comprises the further acts of:
calculating, by the computer device, n-dimensional coordinates associated with a moment of the diploid haplotype pairs of the individual sample;
determining, by the computer device, a distance between coordinates associated with the specific genetic trait class and coordinates associated with the moment; and
identifying that the determined distance for the specific genetic trait class is a minimum relative to determined distances associated with each one of the other genetic trait classes.

15. The method of claim 8, wherein the act of determining that coordinates associated with the individual sample are closest to coordinates associated with a specific one of the genetic trait classes comprises the further acts of:
calculating, by the computer device, n-dimensional coordinates associated with a center of gravity of the diploid haplotype pairs of the individual sample;
determining, by the computer device, a distance between coordinates associated with the specific genetic trait class and coordinates associated with the center of gravity; and
identifying that the determined distance for the specific genetic trait class is a minimum relative to determined distances associated with each one of the other genetic trait classes.

16. The method of claim 8, which is performed by the computer device in accordance with computer instructions stored in a computer readable medium.

17. A computer system for genetically classifying an individual sample outside of a sample population which is based on data of the sample population which includes, for each gene of a plurality of genes, a data table having rows corresponding to a plurality of diploid haplotype pairs in the gene and columns corresponding to a plurality of genetic trait classes of a genetic trait, where each data cell of the data table contains a count of individuals of the sample population that associate with both the corresponding diploid haplotype pair and the corresponding genetic trait class, and, for each table associated with each gene, a first plurality of n-dimensional coordinates for each diploid haplotype pair calculated based on data in the data table, and a second plurality of n-dimensional coordinates for each genetic trait class calculated based on data in the data table, the computer system further comprising:
a computer;
the computer being adapted to calculate, for the individual sample outside of the sample population, n-dimensional coordinates for diploid haplotype pairs of the plurality of genes of the individual sample;
the computer being further adapted to determine that coordinates associated with the individual sample are closest to coordinates associated with a specific one of the genetic trait classes;
the computer being further adapted to produce, based on the determining, a classification decision for the individual sample for classification of the individual sample into the specific genetic trait class; and
the computer being further adapted to output the classification decision for display to a user.

18. The computer system of claim 17, wherein the computer is further adapted to perform a linear or quadratic classification analysis based on the first and the second pluralities of the n-dimensional coordinates.

19. The computer system of claim 17, wherein the computer is further adapted to perform a linear or quadratic classification analysis based on the first and the second pluralities of the n-dimensional coordinates by creating a variance-covariance matrix based on the first and the second pluralities of n-dimensional coordinates determined from the correspondence analysis.

20. The computer system of claim 17, wherein the computer is further adapted to calculate a mass and an inertia for each diploid haplotype pair and for each genetic trait class.

21. The computer system of claim 17, wherein the computer is further adapted to cause one or more plots to be produced for display based on the first and the second pluralities of n-dimensional coordinates, the one or more plots identifying the diploid haplotype pairs and the genetic trait classes.

22. The computer system of claim 17, wherein the computer is further adapted to determine that coordinates associated with the individual sample are closest to coordinates associated with a specific one of the genetic trait classes by:
calculating, by the computer, an average distance between coordinates; and
identifying that the calculated average distance for the specific genetic trait class is a minimum relative to calculated average distances associated with each one of the other genetic trait classes.

23. The computer system of claim 17, wherein the computer is further adapted to determine that coordinates associated with the individual sample are closest to coordinates associated with a specific one of the genetic trait classes by:
calculating, by the computer, n-dimensional coordinates associated with a moment of the diploid haplotype pairs of the individual sample;

determining, by the computer, a distance between coordinates associated with the specific genetic trait class and coordinates associated with the moment; and identifying that the determined distance for the specific genetic trait class is a minimum relative to determined distances associated with each one of the other genetic trait classes.

24. The computer system of claim 17, wherein the computer is further adapted to determine that coordinates associated with the individual sample are closest to coordinates associated with a specific one of the genetic trait classes by:

calculating, by the computer, n-dimensional coordinates associated with a center of gravity of the diploid haplotype pairs of the individual sample;

determining, by the computer, a distance between coordinates associated with the specific genetic trait class and coordinates associated with the center of gravity; and identifying that the determined distance for the specific genetic trait class is a minimum relative to determined distances associated with each one of the other genetic trait classes.

* * * * *